(12) United States Patent
Joshi

(10) Patent No.: US 10,808,211 B2
(45) Date of Patent: Oct. 20, 2020

(54) DISPOSABLE WIPES WITH TREATMENT AGENT SAFELY FORMED INSITU

(71) Applicant: Microlin, LLC, Salt Lake City, UT (US)

(72) Inventor: Ashok V. Joshi, Salt Lake City, UT (US)

(73) Assignee: Microlin, LLC, Salt Lake City, UT (US)

( * ) Notice: Subject to any disclaimer, the term of this patent is extended or adjusted under 35 U.S.C. 154(b) by 73 days.

(21) Appl. No.: 15/953,444

(22) Filed: Apr. 14, 2018

(65) Prior Publication Data

US 2018/0230413 A1   Aug. 16, 2018

Related U.S. Application Data

(63) Continuation-in-part of application No. 15/879,217, filed on Jan. 24, 2018, which is a continuation-in-part
(Continued)

(51) Int. Cl.
*C25B 13/02* (2006.01)
*C25B 9/18* (2006.01)
(Continued)

(52) U.S. Cl.
CPC ............ *C11D 17/049* (2013.01); *A47L 13/17* (2013.01); *A47L 13/19* (2013.01); *A61L 2/186* (2013.01);
(Continued)

(58) Field of Classification Search
CPC ....................................................... C25B 3/00
(Continued)

(56) References Cited

U.S. PATENT DOCUMENTS 5,126,070 A    6/1992   Leifheit et al.
5,335,478 A    8/1994   Aronsen
(Continued)

FOREIGN PATENT DOCUMENTS

EP    2168604       3/2010
EP    2168604 A1    3/2010
(Continued)

OTHER PUBLICATIONS

Extended European Search Report, dated Feb. 17, 2017.
(Continued)

*Primary Examiner* — Zulmariam Mendez
(74) *Attorney, Agent, or Firm* — Brian C. Trask

(57) ABSTRACT

A wipe that can be used deodorize, disinfect, and/or sterilize an object. A wipe manipulator may be used with a wipe to create, energize, or enhance one or more treatment agent in a wipe to improve its efficacy. Desirably, a wipe manipulator is flexible to accommodate to curved surfaces. A wipe includes a flexible membrane or cloth-like element that may apply, distribute, and/or remove a treatment agent to, over, or from a surface of the object. An enhanced treatment agent, such as peracetic acid, may be applied to the surface subsequent to being formed in the wipe as a result of installation of the wipe onto a manipulator, or otherwise activating the wipe. A wipe manipulator may include one or more rechargeable reservoir to contain and apply a synergistic treatment agent to the wipe to create the enhanced treatment agent.

16 Claims, 21 Drawing Sheets

Related U.S. Application Data of application No. 15/435,116, filed on Feb. 16, 2017, which is a continuation-in-part of application No. PCT/US2015/067540, filed on Dec. 27, 2015, which is a continuation-in-part of application No. 14/314,862, filed on Jun. 25, 2014, now Pat. No. 9,603,359.

(60) Provisional application No. 62/164,640, filed on May 21, 2015, provisional application No. 62/098,277, filed on Dec. 30, 2014, provisional application No. 61/839,986, filed on Jun. 27, 2013, provisional application No. 61/846,164, filed on Jul. 15, 2013.

(51) Int. Cl.

| | |
|---|---|
| *C25B 9/04* | (2006.01) |
| *C25B 9/16* | (2006.01) |
| *C25B 11/02* | (2006.01) |
| *C11D 17/04* | (2006.01) |
| *A61L 2/23* | (2006.01) |
| *A47L 13/19* | (2006.01) |
| *A47L 13/17* | (2006.01) |
| *C11D 3/48* | (2006.01) |
| *C11D 3/39* | (2006.01) |
| *B08B 1/00* | (2006.01) |
| *A61L 2/20* | (2006.01) |
| *A61L 2/22* | (2006.01) |
| *A61L 2/18* | (2006.01) |

(52) U.S. Cl.
CPC ............... *A61L 2/202* (2013.01); *A61L 2/208* (2013.01); *A61L 2/22* (2013.01); *A61L 2/23* (2013.01); *B08B 1/006* (2013.01); *C11D 3/3942* (2013.01); *C11D 3/3945* (2013.01); *C11D 3/48* (2013.01); *A61L 2202/11* (2013.01)

(58) Field of Classification Search
USPC ....................................................... 204/242
See application file for complete search history.

(56) References Cited

U.S. PATENT DOCUMENTS

| | | | |
|---|---|---|---|
| 5,407,685 A | 4/1995 | Malchesky et al. | |
| 6,916,480 B2 | 7/2005 | Anderson et al. | |
| 9,433,474 B2 | 9/2016 | Swinney | |
| 2005/0079987 A1 | 4/2005 | Cartwright et al. | |
| 2005/0187580 A1 | 8/2005 | Skiba | |
| 2005/0202066 A1 | 9/2005 | Arata | |
| 2006/0039840 A1 | 2/2006 | Chia et al. | |
| 2010/0078318 A1 | 4/2010 | Huffman | |
| 2011/0118655 A1 | 5/2011 | Fassih et al. | |

FOREIGN PATENT DOCUMENTS

| | | |
|---|---|---|
| EP | 2498867 | 9/2012 |
| JP | 2006-189883 A | 7/1994 |
| WO | 94/26317 | 11/1994 |
| WO | 03-070004 A1 | 8/2003 |
| WO | 2005/107823 | 11/2005 |
| WO | 2011/044355 | 4/2011 |
| WO | 2011059915 | 5/2011 |
| WO | 2014/210164 | 12/2014 |
| WO | 2014210164 | 12/2014 |

OTHER PUBLICATIONS

Nho "Written Opinion of the International Searching Authority" Application No. PCT/US2014/044111, 9 pages, dated Oct. 21, 2014.

Plasma Based Sterilization: Overview and the Stepwise Inactivation Process of Microbial by Non-thermal Atmospheric Pressure Plasma Jet; International Journal of Engineering & Technology IJET-IJENS vol. 14 No. 05.

Surface Micro-Discharge (SMD)—Analysis of the Antimicrobial Effect and the Plasma Chemistry; Dissertation; der Fakultät für Physik der Ludwig-Maximillians-Universität München zur Erlangung des Grades eines Doktors der Naturwissenschaften; Jin Jeon.

Cold Atmospheric Air Plasma Sterilization against Spores and Other Microorganisms of Clinical Interest; Appl Environ Microbiol. Aug. 2012; 78(15): 5077-5082. doi: 10.1128/AEM.00583-12; Tobias G. Klämpfl, Georg Isbary, Tetsuji Shimizu, Yang-Fang Li, Julia L. Zimmermann, Wilhelm Stolz, Jürgen Schlegel, Gregor E. Morfill, and Hans-Ulrich Schmidt.

International Search Report and the Written Opinion of the International Searching Authority, dated Jul. 15, 2016.

International Search report and Written Opinion for PCT/US2015/67540, dated Jul. 15, 2016.

Extended European Search Report, dated Sep. 15, 2017.

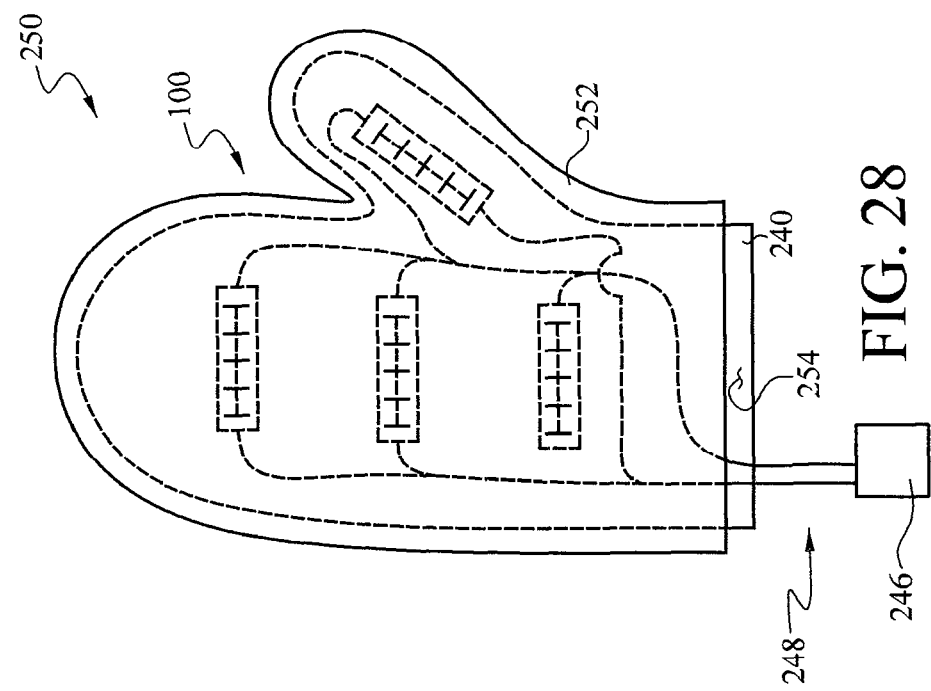
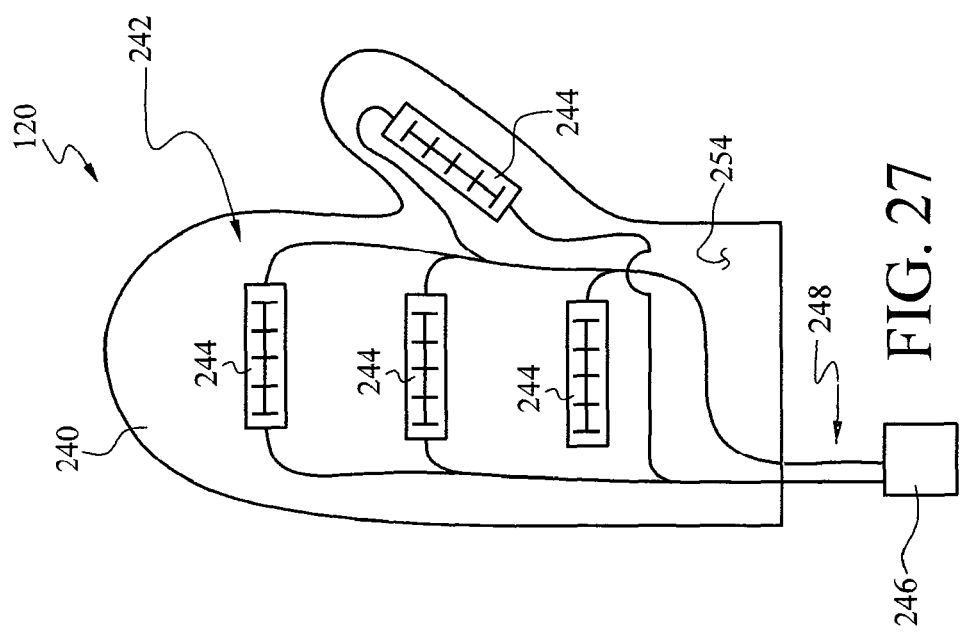
FIG. 28
FIG. 27

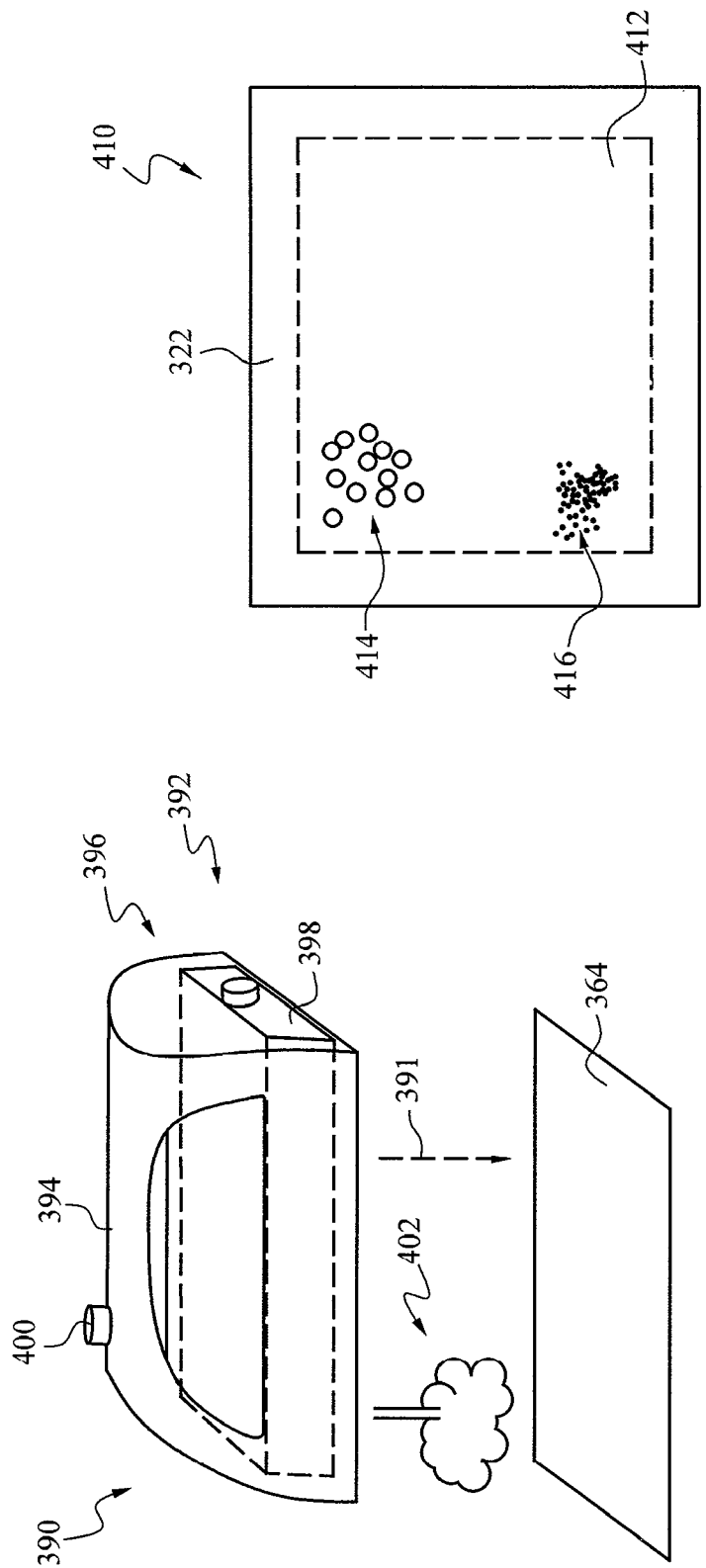

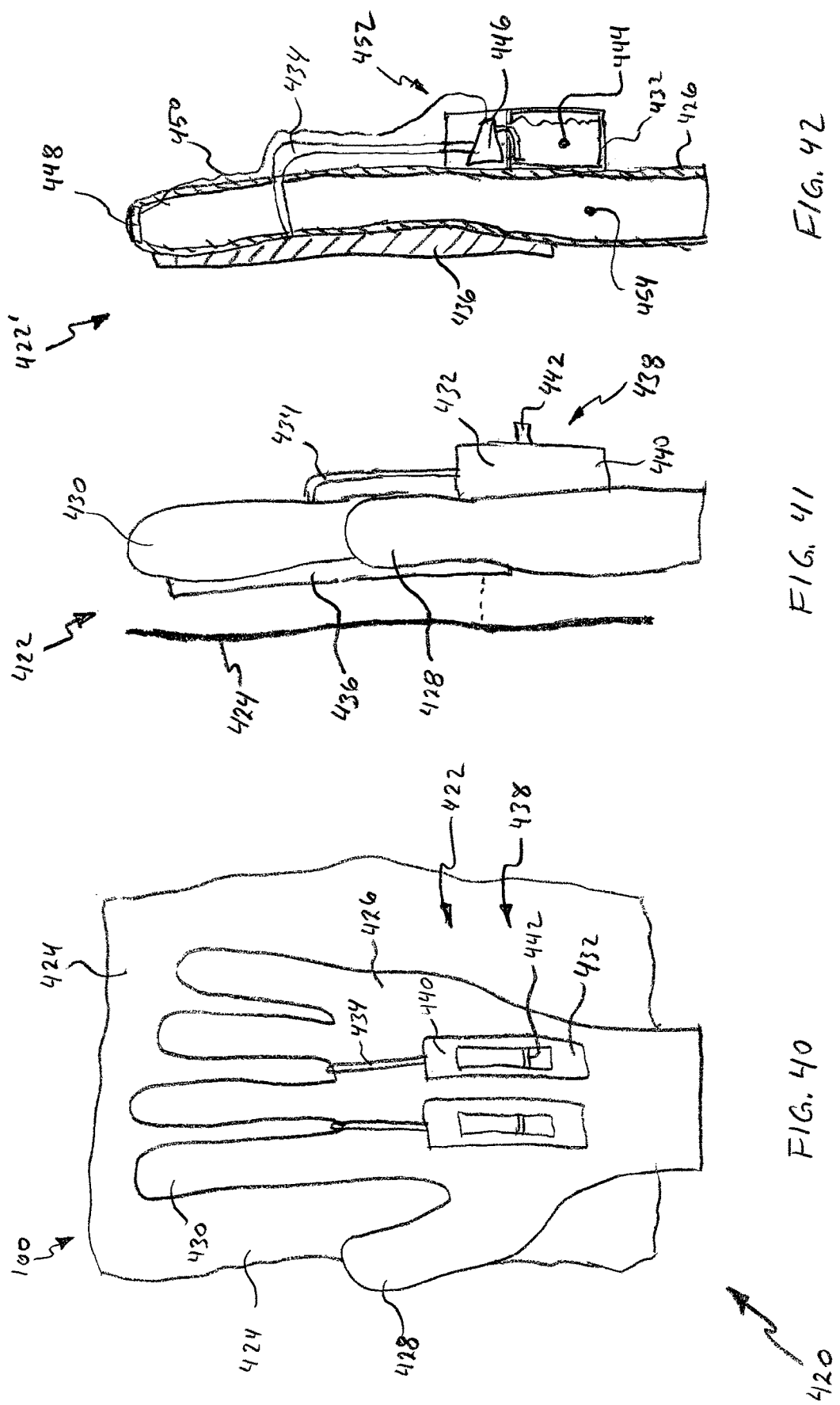

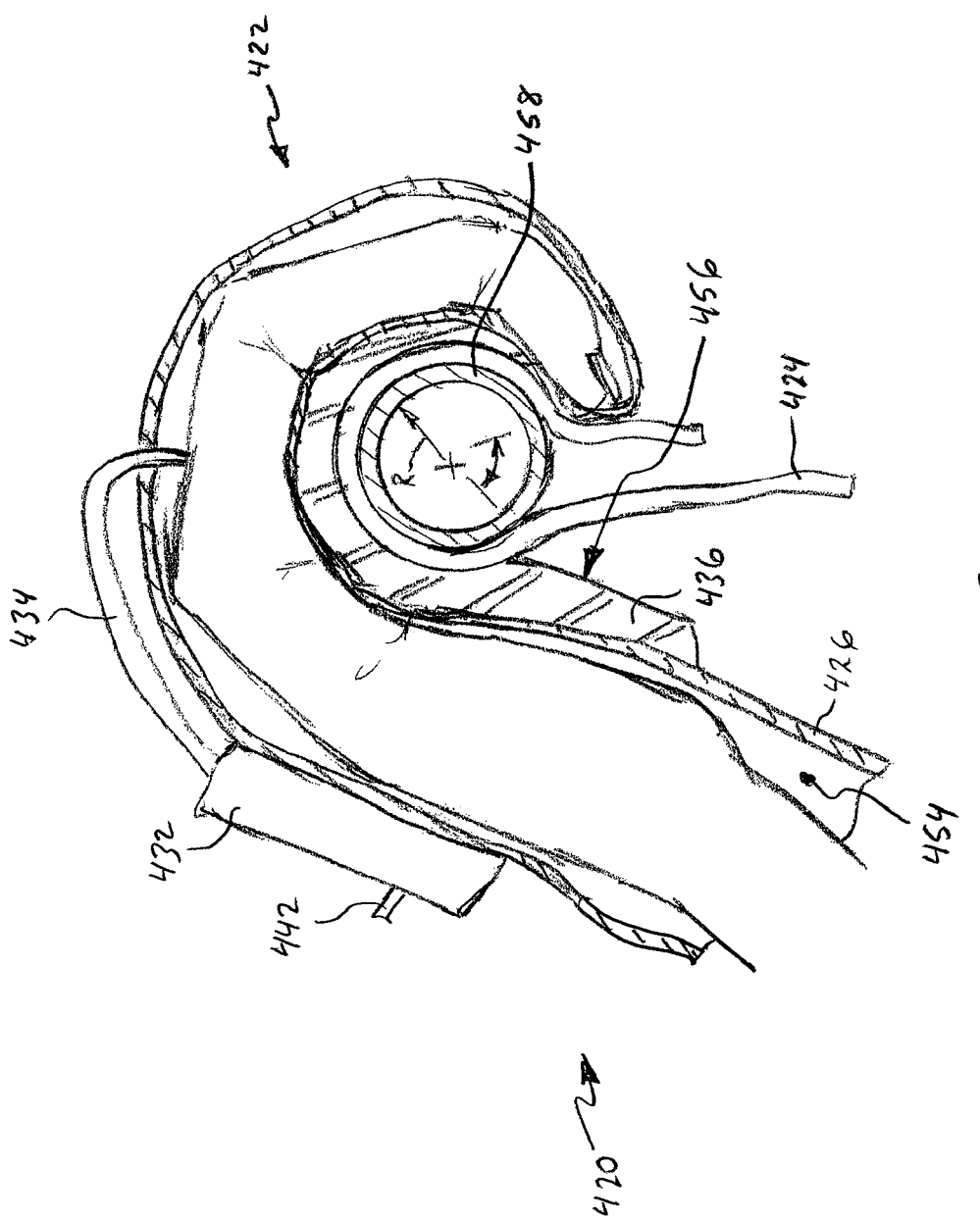

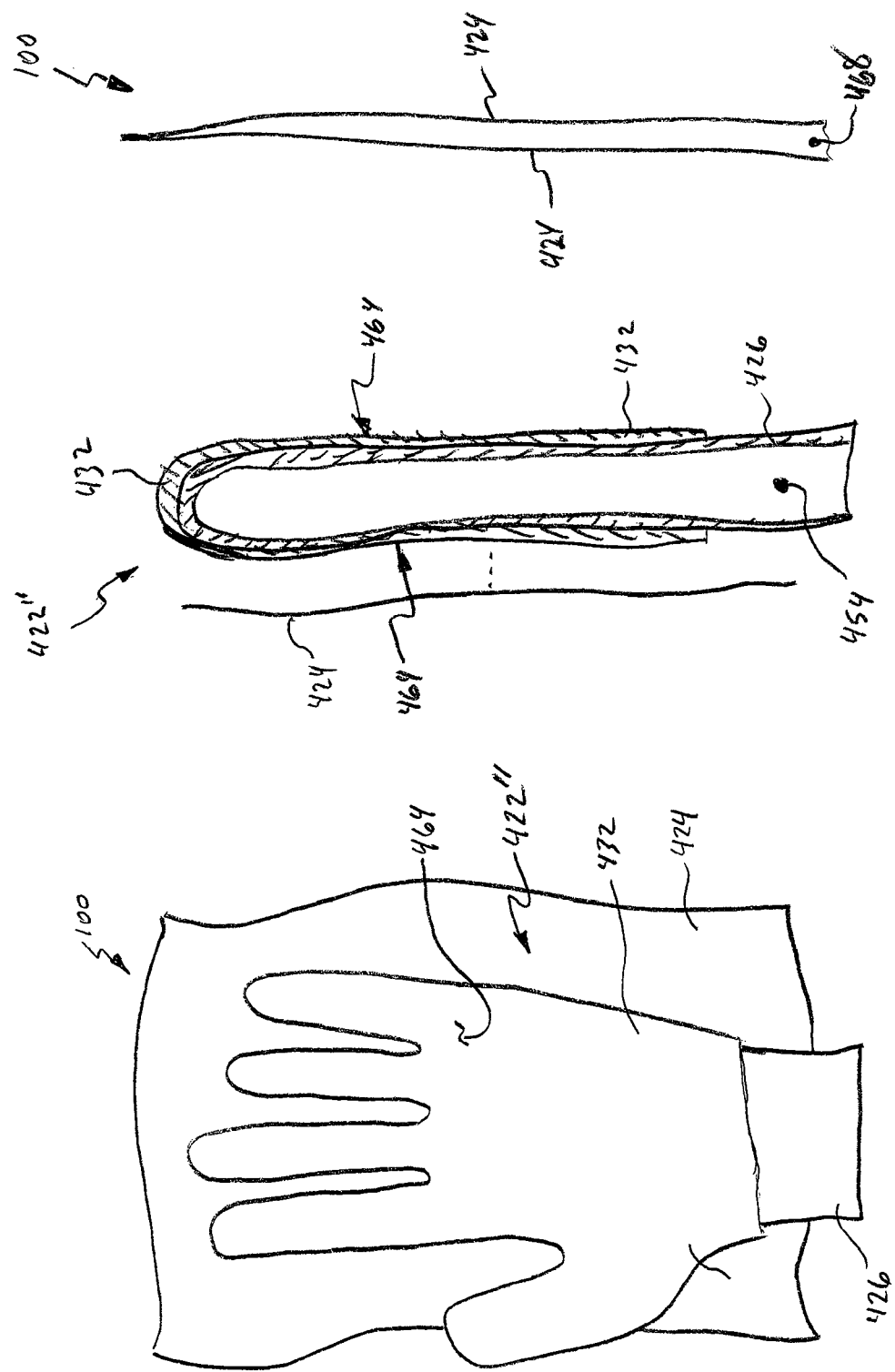

DISPOSABLE WIPES WITH TREATMENT AGENT SAFELY FORMED INSITU

PRIORITY CLAIM

This application is a continuation-in-part of the U.S. utility application Ser. No. 15/879,217, filed Jan. 24, 2018, and titled "DISPOSABLE WIPES WITH PERACETIC ACID TREATMENT AGENT", which is a continuation-in-part of the U.S. utility application Ser. No. 15/435,116, filed Feb. 16, 2017, and titled "DISPOSABLE WIPES FOR ENERGIZED TREATMENT AGENT", which is a continuation-in-part of the International Application Serial No. PCT/US2015/067540, filed Dec. 27, 2015, and titled "DISPOSABLE WIPES FOR OPTIONAL DISINFECTION, DEODORIZATION, AND/OR STERILIZATION AND METHODS OF USE THEREOF", which claims the benefit of the filing dates of U.S. Provisional Patent Application Ser. No. 62/098,277, filed Dec. 30, 2014, entitled "DISPOSABLE WIPES FOR OPTIONAL DISINFECTION, DEODORIZATION, AND/OR STERILIZATION", and Ser. No. 62/164,640, filed on May 21, 2015, and also entitled "DISPOSABLE WIPES FOR OPTIONAL DISINFECTION, DEODORIZATION, AND/OR STERILIZATION"; the application Ser. No. 15/435,116 is also a continuation-in-part of U.S. utility application Ser. No. 14/314,862, titled "ANTI-MICROBIAL DISINFECTANT WIPE AND METHOD OF USE", filed on Jun. 25, 2014, which claims the benefit of the filing dates of U.S. Provisional Patent Application Ser. No. 61/839,986, filed on Jun. 27, 2013, titled "ANTI-MICROBIAL DISINFECTANT WIPE AND METHOD OF USE", and Ser. No. 61/846,164, filed on Jul. 15, 2013, titled "ELECTROCHEMICALLY-ACTIVATED ANTI-MICROBIAL DISINFECTANT WIPE AND METHOD OF USE", each of which is incorporated by this reference as though set forth herein in their entirety.

TECHNICAL FIELD

This invention relates to apparatus and methods for optionally disinfecting, deodorizing, and/or sterilizing various objects by wiping the object with a treatment wipe. Embodiments may include a wipe holder that is structured to improve the efficacy of e.g., commercially available disinfecting wipes. Certain wipe holders energize treatment agent to promote the presence of hydroxyl radicals, or ions, such as Silver ions or chloride ions, or introduce micro-, micron- or nano-sized particles of treatment agent, or peracetic acid, at the time and place of desired treatment. Sometimes, an applicator is used to apply energized treatment agent to a surface or to create the energized treatment agent on a wipe, and a wipe may spread and/or remove treatment agent from the surface.

BACKGROUND

Currently, a wide range of equipment and methods are available to disinfect or sterilize objects and surfaces in residential, industrial, commercial, hospital, hotel, and food processing environments. Exemplary treatment devices for treatment of objects, and methods of use for those treatment devices, are disclosed in U.S. Pat. No. 7,892,486, the entire contents of which are hereby incorporated as a portion of this disclosure by reference. A document disclosing characterization and use of Peroxone as a treatment substance is available on the world wide web at epa.gov/ogwdw/mdbp/pdf/alter/chapt_7.pdf. Although directed generally toward treatment of water, the aforementioned document is also incorporated by reference as a portion of this disclosure. Various chemical reactions and structures for generating Hydroxyl radicals and other deodorizing, disinfecting, and/or sterilizing elements are disclosed in U.S. Provisional Patent Application No. 62/090,799, the entire disclosure of which is also hereby incorporated by reference as a portion of this disclosure.

Unfortunately, the state of the art products and equipment for disinfecting, deodorizing and/or sterilizing are confined to products best suited to use in a commercial or industrial environment, due to increased expense and cumbersome methods and chemicals. In view of the foregoing, what is needed are products, equipment and methods for treating (e.g. disinfecting, deodorizing, and/or sterilizing) surfaces of objects which are simple to use, less expensive, and more environmentally friendly.

DISCLOSURE OF THE INVENTION

The invention may be embodied to provide a one-time-use, disposable wipe for use in optionally deodorizing, disinfecting, or sterilizing an object. An exemplary wipe includes a first substrate comprising a flexible membrane. Typically, a first treatment agent, such as a chemical element or compound, is either associable with, or carried by, the first substrate. A second chemical element or compound may also either be associable with, or carried by, the first substrate. Preferred embodiments are structured to produce peracetic acid at the time of use of the wipe.

In one embodiment, the first substrate is structured to carry a treatment agent formed as a product of a chemical reaction resulting from combination of a first chemical element or compound and a second chemical element or compound at the time of use, and at the location of use, of the wipe to deodorize, disinfect, and/or sterilize an object. In certain preferred embodiments, a wipe carries hydrogen peroxide, a holder carries acetic acid, and an on-the-spot treatment agent includes peracetic acid.

The invention may be embodied in an apparatus including a wipe-holder with a body and a handle affixed to the body. The body can carry a removable reservoir structured to couple with structure associated with the body. A workable reservoir is configured and arranged, upon installation of the reservoir in registration with the body, to dispose a wipe-support surface proud of the body to ensure that a disposable wipe carried there-on will contact a surface to be cleaned or disinfected. In certain embodiments, the reservoir includes a material structured to up-take a liquid first treatment agent and dispense that first treatment agent to a disposable wipe at the wipe-support surface. The wipe-holder is generally used in combination with a disposable wipe to deodorize, disinfect, and/or sterilize a portion of an object at a treatment site.

Generally, the disposable wipe carries a second treatment agent, and the first treatment agent is selected to combine with the second treatment agent to synergistically form a third treatment agent having enhanced biocidal efficacy compared to either the first or second treatment agent, alone. In certain embodiments, first treatment agent is acetic acid, the second treatment agent is hydrogen peroxide, and the third treatment agent is peracetic acid.

One workable reservoir is structured to dispense first treatment agent in misted or vapor phase. An alternative reservoir may be structured to dispense first treatment agent in liquid phase. One currently preferred reservoir includes a styrene-based and/or a butadiene-based polymer or rubber.

A reservoir may include a high surface area material. In certain embodiments, the reservoir is structured as an applicator to dispense treatment agent to a treatment site independent of the presence of a wipe. Sometimes, a reservoir may encompass an absorbent sponge, such as a commercially available cellulose sponge.

A holder may be configured to provide a structural interference between structure associated with the body and structure associated with an installed reservoir. Generally, the holder also includes a retaining mechanism to resist decoupling of the body and reservoir. A preferred holder is structured to dispose a user hand-gripping portion disposed substantially in parallel to the wipe-support surface. In certain embodiments, the holder is compliant to dispose the wipe for contact to irregular and curved surfaces.

The invention may be embodied in a method including providing a wipe-holder, providing a charged reservoir, installing the charged reservoir in registration with the body with the reservoir providing a wipe-support surface; and using the holder in combination with an installed disposable wipe to rub the wipe over a surface to clean and/or to disinfect that surface. Typically, the holder and wipe combine to form a synergistic treatment product, such as peracetic acid. The method may also include removing the reservoir from the body, and placing the removed reservoir into a quantity of treatment agent in a recharging step to recharge the reservoir. The recharged reservoir may then be reinstalled in registration with the body. Preferably, the recharging step is carried out at substantially room temperature.

The recharging step may include adsorbing treatment agent into a portion of the reservoir. The recharging step may include absorbing the treatment agent into a portion of the reservoir. The recharging step may include uptake of treatment agent by a portion of the reservoir through a diffusion, or other essentially atomic, or molecular-scale process. In a preferred method, the recharging step includes placing the reservoir into a quantity of household vinegar.

The invention may be embodied in a method including providing a wipe-holder structured in harmony with a disposable wipe to modify a first treatment agent carried by the wipe. A first treatment agent may be selected from the group consisting of hydrogen peroxide and sodium peroxide. The method may include forming peracetic acid from a portion of the first chemical treatment agent. The wipe-holder may include a reservoir to dispense a second treatment agent, such as acetic acid, to the disposable wipe. The method may also include placing a disposable wipe in operable registration with the reservoir to form an enhanced treatment agent, such as peracetic acid. A further step includes treating a surface of an object by moving the holder to rub the surface with the enhanced treatment agent formed in the disposable wipe as a product of the first treatment agent and the second treatment agent. Subsequently, the reservoir may be removed and recharged (e.g., with acetic acid) as desired.

In one embodiment of a wipe, the first chemical element or compound is carried by a first substrate, and the second chemical element or compound is also carried by the first substrate. Desirably, the first and second chemical element or compound are selected from chemically reactive couples structured such that fluid applied to the first substrate is effective to cause a chemical reaction, and consequently, to produce a treatment agent. A workable fluid may include water. The first chemical element or compound and the second chemical element or compound can be selected a make a couple set forth in the group consisting of (Sodium Chlorate and Citric acid; Citric acid and Silver Citrate; Alkali-Percarbonate and Magnesium Oxide; Sodium Chlorite and Citric acid; Quaternary Ammonium Salt and Calcium Hypochlorite; Alkali-perchlorate and UV light; Silver Chloride and UV light; Iron Sulfate and Alkali-percarbonate; stable Hydrogen Peroxide and Iron Sulfate; Hydrogen Peroxide and Acetic acid; Hydrogen Peroxide and Silver Nitrate; and Hydrogen Peroxide and Alcohol, specifically including Benzyl alcohol).

In another embodiment, the first chemical element or compound is carried by the first substrate, and the second chemical element or compound is carried by a dispenser independent from the first substrate. That dispenser is generally structured to apply the second chemical element or compound to the substrate. Again, the first and second chemical element or compound may be selected from chemically reactive couples such that application of the second chemical element or compound by the dispenser to the first substrate is effective to cause a chemical reaction that forms a treatment agent. A preferred treatment agent includes peracetic acid.

In another embodiment, both of the first and second chemical element or compound are carried by a dispenser independent from the first substrate. The dispenser can be structured to apply the first and second chemical element or compound to the first substrate to form an activated wipe. Again, the first and second chemical element or compound are typically selected from chemically reactive couples such that application of the first and second chemical element or compound by the dispenser to the first substrate is effective to cause the chemical reaction. One exemplary dispenser includes a spray bottle, which can be a multi-compartment bottle. Another dispenser can be incorporated into a handle that can be used to hold and operate the wipe during a cleaning process.

Sometimes, a biocidal compound or element may carried on a wipe, or otherwise introduced to a treatment area by an applicator. A workable biocidal compound or element may be selected from the group including (Triclosan; Chlorine dioxide; Hydroxyl radicals; Silver citrate; Sodium Chlorate or Sodium Chlorite; Alkali percarbonate; or Sodium dichloroisocynurate; and quaternary ammonium compounds).

In another embodiment, a wipe may be formed by stacking in physical contact, or juxtaposing, a plurality of substrates. For example, a first chemical element or compound may be carried by a first substrate, and a second chemical element or compound may be carried by a second substrate. Desirably, the first and second chemical element or compound are selected from chemically reactive couples structured such that juxtaposition of the first and second substrates in the presence of moisture can be effective to cause a chemical reaction that produces a desired treatment agent. Sometimes, the chemical reaction may further require application of moisture to the wipe.

A multi-layer wipe may be formed by extraction of a plurality of prepared substrates from one or more dispenser. In one example, a dispenser may include a first chamber and a second chamber. The first chamber may hold a plurality of flexible substrates, each such substrate being removable from the first chamber to form a first substrate. The second chamber can also hold a plurality of flexible substrates, each such substrate being removable to form a second substrate. In a preferred arrangement, a dispenser is structured to facilitate simultaneous dispensation of substrates from a first compartment and a second compartment to automatically produce successive sets of juxtaposed first and second substrates. In certain embodiments, one or both of the first and second chambers may contain excess fluid to maintain the respective substrates in a damp condition. In a preferred embodiment, a first chamber holds Hydrogen peroxide wipe substrates, and a second chamber holds acetic acid wipe substrates. Therefore, a combined pair of substrates automatically creates a multi-layer wipe that forms peracetic acid at the time the respective substrates are combined. Sometimes, paired substrates may be dispensed in damp condition, ready for use. Other times, paired substrates may be wetted by a fluid prior to use.

A wipe may sometimes be used with a holder structured to facilitate or cause a chemical reaction that makes a treatment agent. Sometimes, a holder may operate on a treatment agent to place the agent into a more reactive, or effective form. For example, a holder may cause a treatment agent to be dispersed into micro-, micron-, or nano-sized particles that may then be applied to the surface to be treated.

A wipe may also, or alternatively, be used with a holder structured to impart an electrical charge onto the wipe, and/or introduce a plasma to the wipe and its treatment agent effective to produce a chemical compound in radical form. A holder may even be configured to permit a plasma, or an alternative output from an energizing transducer, to participate in treatment of an object for deodorizing, disinfecting, and/or sterilizing. In certain cases, a biocidal agent may be advantageously included in the wipe. Sometimes, a wipe includes or carries a biocidal agent, and also may be structured to cause an on-board electrical charge generation operable to attract gram positive and/or negative microbes to the biocidal agent.

In an alternative embodiment, an applicator may be employed to cause a fluidized treatment agent to be dispersed into micro-, micron-, or nano-sized particles that may then be applied to the surface to be treated, and a wipe may be used to spread the treatment agent and/or remove the agent from the surface. In that case, a wipe may be embodied in a simple paper towel, cotton cloth, or in some other fluid-absorbent membrane-like element.

Certain wipes can be used by activating a wipe to cause a chemical or physical reaction, and treating an object by physically spreading an energized treatment agent (e.g., scrubbing a surface of the object), formed as a product of a chemical reaction or as a consequence of a physical change imparted to the treatment agent, onto the object with the wipe.

On the other hand, certain wipes may be substantially inert. An exemplary inert wipe may be used to spread energized treatment agent over, and/or remove energized treatment agent from, a surface. Preferred treatment agents include peracetic acid, Hydroxyl radicals and micron- or nano-sized particles of disinfectant chemicals. Operable disinfectant chemicals may include an Alcohol, Hydrogen Peroxide, Ammonium Quaternary compounds, or bleaches such as Sodium Hypochlorite. A biocidal agent may be included in a wipe to further enhance destruction of bacteria and microbes.

An embodiment forms an apparatus for cleaning, deodorizing, disinfecting, or sterilizing a surface of an object. One embodiment includes a wipe to apply a first treatment agent to treat the object, the wipe to form the first treatment agent in the wipe at the time and place of use of the wipe. Desirably, but not always, the wipe is disposable. In some cases, the first treatment agent is unsafe for direct contact with human skin.

The wipe may be used in combination with a wipe manipulator to move the wipe over the surface. A workable wipe manipulator may include a safety mechanism to resist formation of the first treatment agent until a user's hand is protected from contact with the first treatment agent. Sometimes, a wipe manipulator may be structured to apply a second treatment agent for combination with a third treatment agent, the second treatment agent and third treatment agent combining to form the first treatment agent.

A workable first treatment agent may be selected from the group including Hydrogen Peroxide, peracetic acid, Chlorine Dioxide, Sodium Hypochlorite, Hydroxyl radicals, Glutaraldehyde, Phenol, a mixture of two or more elements from this group, and the like. A second treatment agent may include an element selected from the group of Acetic acid, vinegar, tetraacetylethylenediamine (TAED), and a mixture of two or more elements from this group. A currently preferred third treatment agent includes Hydrogen peroxide. One currently preferred first treatment agent is Peracetic acid.

A workable second treatment agent includes solid mixtures of Sodium acetate and Benzoic acid, or Sodium acetate and Citric acid. In those cases, a cooperating third treatment agent includes Hydrogen Peroxide, and a resulting first treatment agent is Peracetic acid.

In another arrangement, a second treatment agent may be Sodium Chlorite or Sodium Chlorate in liquid solution. A cooperating third treatment agent is then a mild acid, such as Citric acid or dilute Hydrochloric acid, and the resulting first treatment agent is Chlorine Dioxide.

In other cases, the second treatment agent can include an element selected from the group including UV light, Ferrous Sulfate, and Ozone. A cooperating third treatment agent is Hydrogen Peroxide, and the resulting first treatment agent is Hydroxyl radicals.

Some embodiments of a wipe manipulator may include a first reservoir. A first reservoir can hold a quantity of a second treatment agent for combination with a third treatment agent carried by the wipe, and the second treatment agent and the third treatment agent may combine to form the first treatment agent. Certain wipe manipulators may carry a first reservoir and a second reservoir, the first reservoir to hold a quantity of a second treatment agent, the second reservoir to hold a quantity of a third treatment agent, the second treatment agent and the third treatment agent combining to form the first treatment agent. The first reservoir may sometimes hold a quantity of a second treatment agent in liquid solution. It is within contemplation that a wipe manipulator may carry a plurality of reservoirs to hold a plurality of different fluids, elements, or compounds for application to a wipe.

The first reservoir may hold a quantity of a second treatment agent and be structured to permit off-gas application of the second treatment agent from the first reservoir to combine with a third treatment agent to form the first treatment agent in the wipe.

Desirably, the wipe manipulator includes a wipe support surface that is transversely flexible to accommodate wiping a curved surface. A workable wipe manipulator may include a portion of a glove or mitten. Sometimes, a wipe manipulator may carry, or inherently possess, a discharge mechanism to dispense the second treatment agent at a desired rate and quantity. In some cases, the wipe manipulator may include a safety mechanism that normally disposes a structural barrier between a user's hand and a location of formation of the first treatment agent. A wipe manipulator may carry one or more of a mechanical actuator, switch, controls, and other electronic elements, power source, and the like, to permit a user to effect discharge of a treatment agent on-demand.

Certain embodiments include a wipe manipulator to move a wipe over the surface of an object to be treated, the wipe manipulator being structured to carry and apply a second treatment agent for combination with a third treatment agent, the second treatment agent and third treatment agent combining to form the first treatment agent, the wipe manipulator including a safety mechanism to resist formation of the first treatment agent until a user's hand is protected from contact with the first treatment agent, the wipe manipulator further including a wipe support surface that is sufficiently transversely flexible as to enable using the wipe support surface to wrap a wipe around about 270 degrees of the circumference of a curved surface of a ½ inch diameter rod.

A workable wipe manipulator may be structured as a glove or mitten to receive a human hand in a substantially enclosed volume. A wipe manipulator may also include an exposed surface of a first reservoir to support a wipe and formed from a material capable of temporarily and internally holding a second treatment agent to permit off-gas release of the second treatment agent for combination with a third treatment agent in the wipe, the second treatment agent and third treatment agent combining to form the first treatment agent.

BRIEF DESCRIPTION OF THE DRAWINGS

In the drawings, which illustrate what are currently regarded as the best modes for carrying out the invention:

FIG. 27 is a pictorial view of a workable energizing wipe holder that is compliant to accommodate to irregular or non-flat surfaces;

FIG. 28 illustrates a wipe installed on the embodiment of FIG. 27;

FIG. 38 is a view in perspective of another alternative wipe holder and wipe;

FIG. 39 illustrates another wipe;

FIG. 40 is a top plan view of a wipe and a wipe manipulator;

FIG. 41 is a side view of the embodiment in FIG. 40;

FIG. 42 is a side view, partially in cross-section, of the embodiment illustrated in FIG. 41;

FIG. 43 is a side view in section of the embodiment in FIG. 40 illustrated in use to treat a cylinder;

FIG. 44 is a plan view of an alternative embodiment of a wipe manipulator and a wipe;

FIG. 45 is a side view in section of the embodiment of FIG. 44; and

FIG. 46 is a side view in section of an alternative wipe structured as a pocket or mitten.

DETAILED DESCRIPTION OF THE ILLUSTRATED EMBODIMENTS

Certain preferred embodiments are structured to apply one or more treatment agent to a surface for purpose of cleaning, disinfection, deodorization, and/or sterilization of that surface. Treatment agents may nonexclusively include one or more of Hydroxyl radicals, Hydrogen peroxide, acetic acid, peracetic acid, biocidal agent, and the like. One embodiment according to certain principles of the invention may be characterized as a Fenton cleaning wipe. Desirably, a cleaning wipe is a low-cost element, and can therefore be discarded after a single use. A wipe may be structured for activation at the time of use to generate one or more treatment agent at the location of use of the wipe to treat an object.

An exemplary Fenton cleaning wipe includes two or more reactive chemical electrodes, which may be carried by a body formed from flexible polymeric or cellulosic material. A workable body may be structured as a flexible membrane made from e.g., paper, cloth, sponge, sponge-like materials, and the like. The chemicals may be carried on the body, embedded in the body, or carried in one or more pockets formed in the body, or the like. Typically, the electrodes are separated from each other in some fashion, such as by a space, gap, or divider formed by sufficiently inert material. Sometimes, one electrode is carried on the body, and a mating pair element to that electrode is applied by an applicator. When activated (e.g., by moisture such as tap water, or a reactive fluid), the electrodes react with each other and generate a cleaning solution that can be applied to a surface or object. Depending on the amount of reactive chemicals present, the wipe can be used for deodorization, disinfection or sterilization. Sometimes, a wipe may include abrasive materials to facilitate deeper cleaning of a surface or object.

Figure 1:
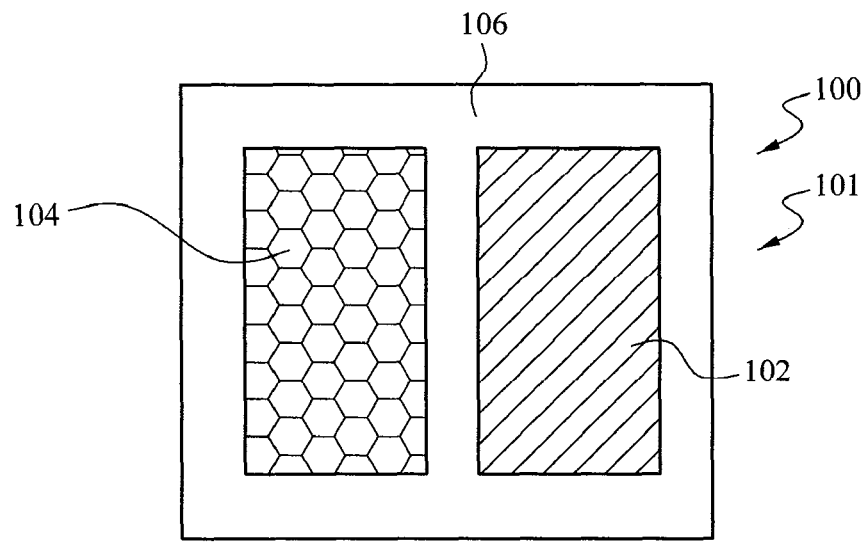
FIG. 1 is a pictorial view in elevation of a first disposable treatment wiper structured according to certain principles of the instant invention.

An exemplary treatment wipe, generally 100, is illustrated in FIG. 1. The treatment wipe 100 in FIG. 1 is a two-electrode embodiment, generally 101, and includes first electrode 102 and second electrode 104 carried by a body 106. First electrode 102 may include a percarbonate compound, such as any alkali-percarbonate. Second electrode 104 may include a Fenton catalyst, such as Iron sulfate ($FeSO_4$) or Iron sulfite ($FeSO_3$). Either one or both of electrodes 102, 104 may be essentially painted-on, or somehow printed-onto or adhered to, body 106. It is alternatively within contemplation that the electrodes 102, 104 can variously be embedded into, or carried in compartments formed in, the body 106.

A body 106 may be formed as a single or multi-layer structure. In the latter case, one side or layer may be structured to provide a barrier (such as a moisture, or chemically-resistant, barrier) between a user's hand and the reactive compounds to be applied to a surface. The other side may be structured to facilitate communication of water or reactive fluid between the electrodes 102, 104, and/or application of one or more treatment agent onto the object to be treated. One or more pocket may be formed between layers in which to hold substances that may form treatment agents.

A treatment wipe 100 may include a variety of different electrode pairs or reactive chemical couples. For non-limiting examples, pairs of electrodes may include: Sodium Chlorate and Citric acid; Citric acid and Silver Citrate; Alkali-Percarbonate and Magnesium Oxide; Sodium Chlorite and Citric acid; Quaternary Ammonium Salt and Calcium Hypochlorite; Alkali-perchlorate and UV light; Silver Chloride and UV light; Iron Sulfate and Alkali-percarbonate; stable Hydrogen Peroxide and Iron Sulfate; Hydrogen Peroxide and Silver Nitrate; Hydrogen Peroxide and one or more Alcohol such as Benzyl alcohol, Methyl alcohol, Ethyl alcohol, and the like; a biocidal conducting electrode with a positive electrical charge dispenser; a biocidal conducting electrode with a negative electrical charge dispenser; and a pair of biocidal conducting electrodes with cooperating positive and negative electrical charge dispensers to simultaneously attract and kill both gram positive and gram negative bacteria or microbes.

Activation of a chemical reaction to produce a treatment reaction product or agent (e.g. a biocidal disinfecting or sterilizing agent) is typically accomplished at the time of a treatment. Wipes may be stored in a substantially inert form, and activated just before, or during, use to treat an object. Activation may sometimes be accomplished by application of a fluid to the dry electrodes 102, 104. Operable fluids can include tap water or sometimes a fluidized chemical reagent. Certain embodiments may include, or otherwise be associated with, an optional UV light or chemical element such as Ozone. Further, one or more abrasive material may be applied to, or included with, one or more of the electrodes 102, 104. It is within contemplation to include a catalyst to promote reaction speed for the resulting chemical reaction of the above-listed and alternative operational pairings or couples. It is further within contemplation to include one or more additional agent to enhance biocidal activity of an electrode 102 or 104. For example, Triclosan may be included in any one of the electrodes.

Figure 2:
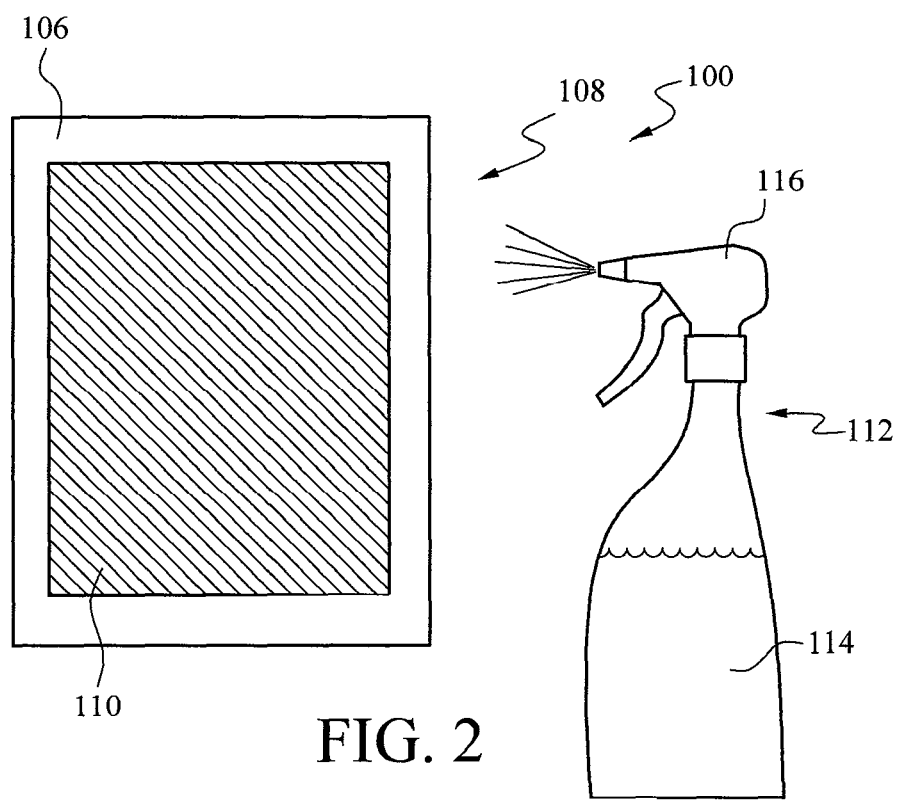
FIG. 2 is a pictorial view in elevation of a second disposable wiper, in combination with a spray bottle of solution.

Alternative embodiments of a wipe 100 may include a single dry electrode including one electrode of the above-listed electrode pairs, and a fluidized activation agent including a mating chemical electrode compound to the dry electrode. The wipe 100 illustrated in FIG. 2 is exemplary of such a single-electrode wipe, generally indicated at 108. Wipe 108 has a single electrode 110 carried on wipe body 106.

A fluid source, generally 112, carries a cooperating reactive substance 114 to generate a treatment agent (which may include biocidal compounds, such as Hydroxyl radicals), when combined with electrode 110. A workable fluid source 112 includes spray bottle 116. For example, if the electrode 110 includes an alkali-percarbonate, a cooperating fluid substance 114 may be a Fenton catalyst in solution, such as Iron Sulfate. In a different case, the single electrode wipe 108 may carry a dry citric acid while the spray device 112 may apply a Sodium Chlorite solution onto the wipe 108 at the time and point of use to create a biocidal Chlorine dioxide compound for deodorization, disinfection, and/or sterilization of an object.

It should be understood that a wipe 100, 101, 108 is typically used as a device operable to spread or apply one or more treatment agent onto the surface of an object. Part of a wipe 100 may apply a fluid to an object to be treated, and another part of the wipe 100 may absorb the fluid along with undesired elements.

Figure 3:
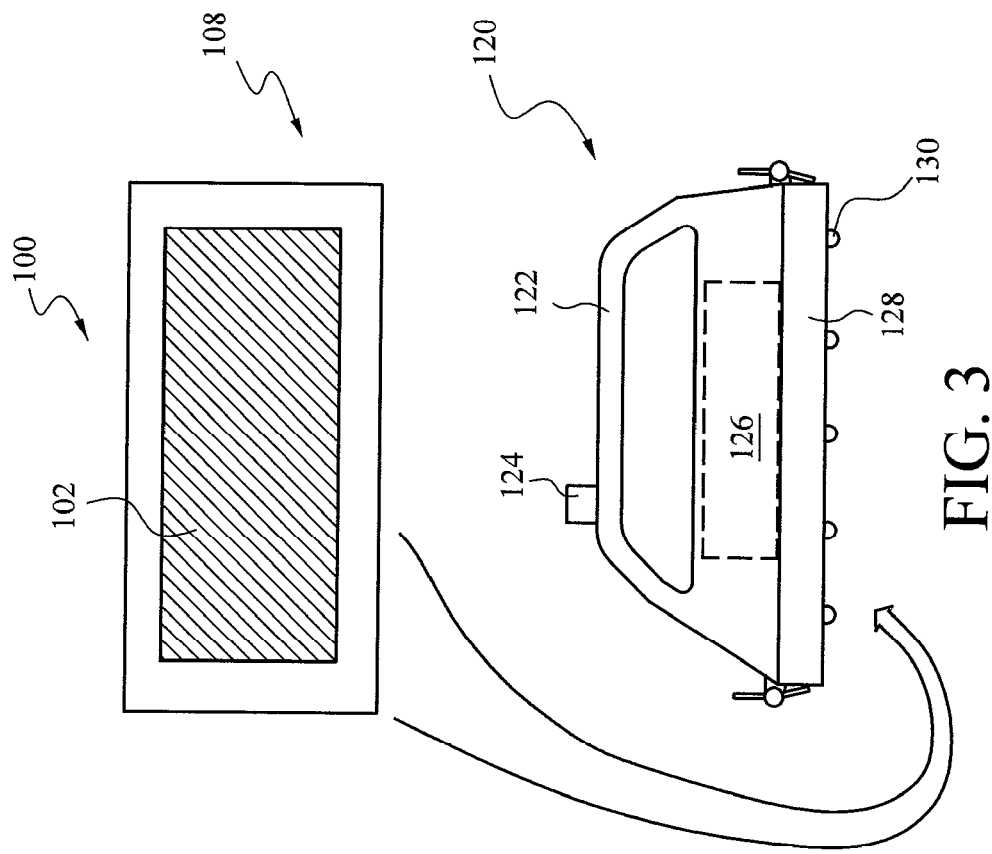
FIG. 3 is a pictorial view in elevation of a third disposable wipe, in combination with a Hydroxyl radical-generating wipe-holder.

As indicated in FIG. 3, a disposable wipe 100, such as the one-electrode wipe 108, may be carried by a re-usable wipe-holder, generally indicated at 120. The one-electrode wipe 108 may be considered as a disposable cleaning element, somewhat like a commercially available "Swiffer Sweeper"™, but more aggressive in that the wipe 108 can also disinfect and/or sterilize a surface. A workable wipe holder 120 may simply stretch the wipe 108 into a planar, or any other desired, shape. Another operable wipe-holder 120 may include a spray device to introduce moisture (including tap water) or a reactive element to interact with one or more compound carried by a wipe 108.

The wipe-holder 120 illustrated in FIG. 3 includes a short horizontal handle 122 structured to hold in a user's hand, like an iron. It is within contemplation that a handle 122 may be configured for any particular use. For example, an alternative handle 122 may be embodied as an elongate shaft, like a broomstick or mop handle.

The illustrated wipe-holder 120 also includes a switch 124 that couples a power source, such as batteries 126, to operate a UV light 128. In combination with an exemplary wipe 108 that carries e.g. Sodium- (or other Alkali-) percarbonate or perborate, the holder 120 can generate Hydroxyl radicals to deodorize, disinfect, and/or sterilize a surface or object. A fluid source may also be included in a holder 120 to introduce moisture or a reactive element to a wipe 108. Sometimes, a wipe holder 120 may include one or more catalyst 130. Currently preferred catalyst materials include Nano Titanium Oxide and Nano Gallium Nitride wires or tubes.

An alternative holder 120 for a wipe 100 may include a surface corona discharge unit for UV generation, and/or ozone generation. A further alternative holder 120 may generate Ozone. The Ozone generator provides and directs Ozone to react with a chemical compound carried by a wipe 100, which in turn, generates disinfecting or sterilizing fluid in the wipe. Another alternative holder 120 within contemplation generates high temperature steam, which may be applied to either or both of the wipe 100 and surface to be treated. A still further alternative holder 120 may dispense an Iron-based catalyst to interact with a chemical compound carried on a disposable wipe 100. A Fenton reaction may thereby be created in the wipe 100 to produce Hydroxyl radicals for treatment of the desired surface or object.

Another alternative holder 120 for a wipe 100 includes an electrical charge delivery capability to a wipe 100 that is coated with electrical conducting materials, including metals and nonmetals. One operable embodiment 100 can be coated with carbon, or carbon paper may form the wipe itself. Most microbial cells and biological surfaces are negatively charged. In a fluid environment, a positively charged wipe 100 attracts negatively charged bacteria and microbes, and vice versa. If the wipe 100 contains a biocidal chemical, then attracted or otherwise-encountered bacteria or microbes will be killed. For example, if a treatment wipe 100 has a biocidal agent (such as Silver citrate; Sodium Chlorate or Sodium Cholite; Alkali percarbonate; or Sodium dichloroisocynurate) disposed in an electrically conductive electrode, then putting an electric charge on such a wipe will attract and kill oppositely charged bacteria or microbes at, or sufficiently near to, that electrode. In alternative arrangements, simply scrubbing or rubbing a surface with a disposable wipe 100 may cause same-charge bacteria or microbes to encounter the killing zone associated with a biocidal agent and its electrode, or the wipe 100, itself.

Figure 4:
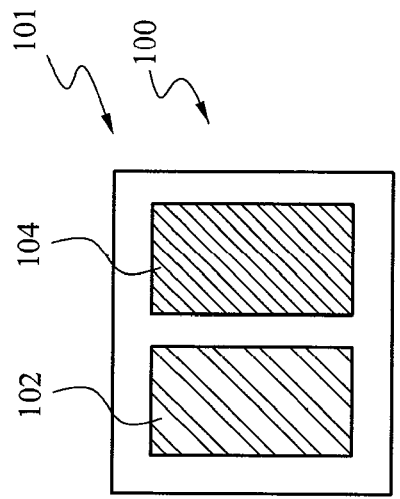
FIG. 4 is a pictorial view in elevation of a fourth disposable wipe.
Figure 5:
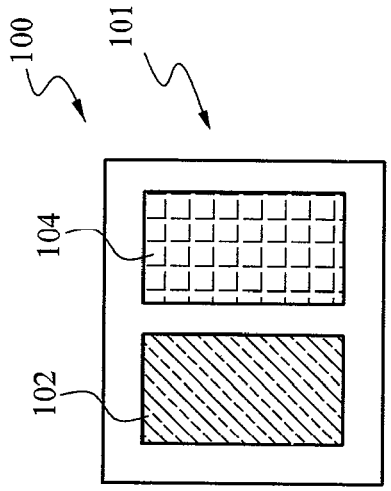
FIG. 5 is a pictorial view in elevation of a fifth disposable wipe.
Figure 6:
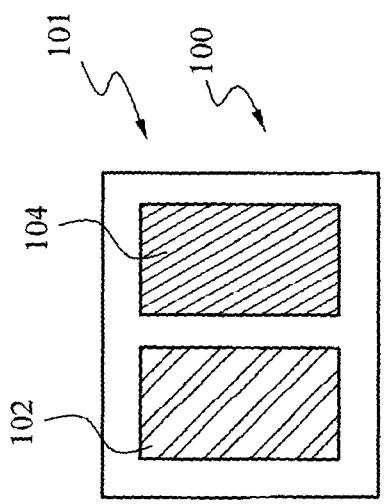
FIG. 6 is a pictorial view in elevation of a sixth disposable wipe.

FIGS. 4-8 illustrate a variety of workable configurations for a disposable wipe 100. Typically, the electrode(s) is/are imparted a sufficient amount of fluid, such as tap water or other activation agent, to initiate a reaction to form an active ingredient that can deodorize, disinfect, and/or sterilize a surface or object. The two-electrode wipe 101 in FIG. 4 illustrates the case when first electrode 102 includes a percarbonate, and second electrode 104 includes Magnesium oxide ($MgO_2$). The two-electrode wipe 101 in FIG. 5 illustrates the case when first electrode 102 includes a percarbonate (such as Sodium percarbonate), and second electrode 104 includes Citric acid, which can sometimes be essentially painted onto the wipe 100. FIG. 6 illustrates the case when first electrode 102 includes Citric acid, and second electrode 104 includes Silver Citrate.

Figure 8:
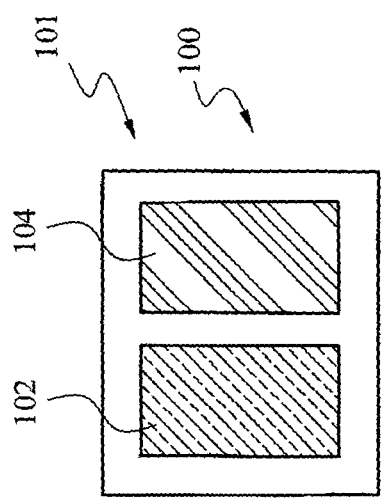
FIG. 8 is a pictorial view in elevation of a eighth disposable wipe.
Figure 7:
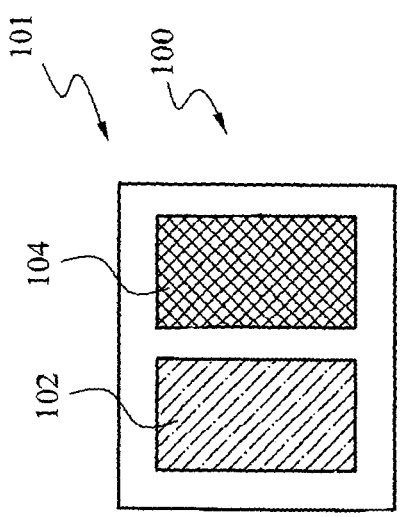
FIG. 7 is a pictorial view in elevation of a seventh disposable wipe.

FIG. 7 illustrates the case when first electrode 102 includes Sodium Chlorite, and second electrode 104 includes Citric acid. Again, the electrodes may be painted onto the wipe 100, and then dried for storage and transportation to a site of use. Upon wetting, the electrodes of wipe 100 in FIG. 7 combine to form Sodium Citrate plus Chlorous acid ($HClO_2$). FIG. 8 illustrates first electrode 102 including Sodium Chlorate, and second electrode 104 includes Citric acid. Upon wetting, the two electrodes of wipe 100 in FIG. 8 combine to form Sodium Chlorate ($NaClO_3$).

Figure 9:
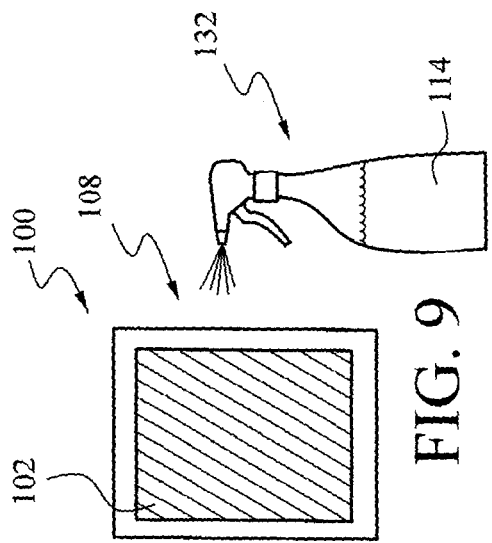
FIGS. 9 through 13 are pictorial views in elevation of additional disposable wipes, each wipe being in combination with a spray bottle of solution.
Figure 11:
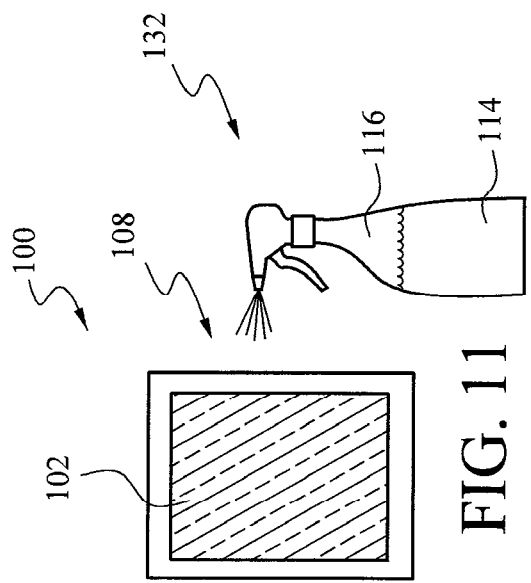

The single-electrode embodiments 108 in FIGS. 9-12 illustrate workable combinations of a disposable treatment wipe 100 that carries one or more chemical compound, and a fluidized activation agent, generally 132, that is combined with the wipe 100. In FIG. 9, electrode 102 may be made from, or include, Citric Acid that is painted, or otherwise applied to the single-electrode wipe 108, and then dried. A cooperating fluidized substance 114 may include: Sodium Chlorite; Sodium Chlorate; Calcium Chlorate; and/or Calcium Chlorite. Electrode 102 in FIG. 10 may similarly be, or include, Citric Acid, and activation substance 114 may be an Alcali-Percarbonate. FIG. 11 illustrates the reverse situation, where electrode 102 may be, or include, an Alcali-Perchlorate, and activation substance 114 includes Citric acid. Electrode 102 in FIG. 12 may be, or include, Calcium hypochlorite, and cooperating activation substance 114 may include an Iron (II) Sulfate solution ($FeSO_4$).

Figure 12:
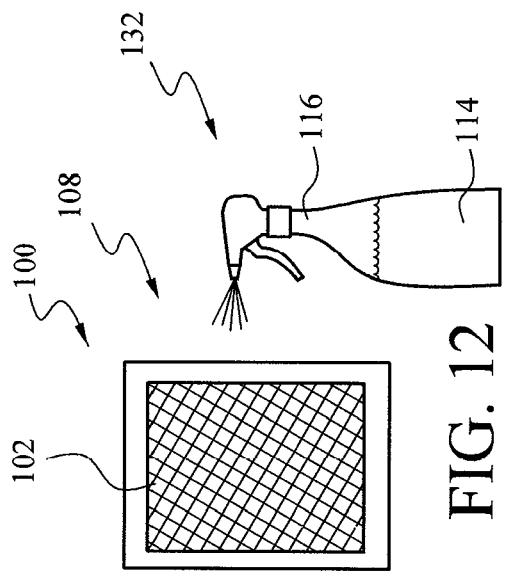
Figure 10:
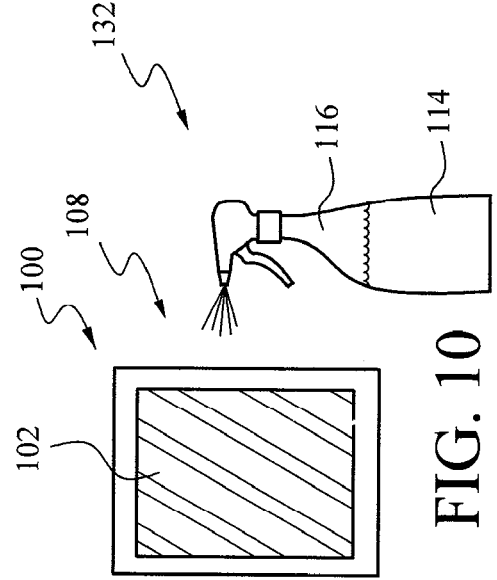

An exemplary alternative embodiment also illustrated by FIGS. 10-12 includes a commercially available damp wipe 100 that carries Hydrogen peroxide as a first treatment agent. A spray bottle 116 may be used to apply another treatment agent (such as acetic acid or glycolic acid) included in compound 114 to the wipe 102 to form a third treatment agent, such as peracetic acid.

Another alternative embodiment illustrated by FIGS. 10-12 includes the case where wipe 100 carries a chemical compound that can form a first treatment agent, or maybe is a first treatment agent, and a cooperating substance 114 that releases, activates, or makes available, the first treatment agent. Sometimes the substance 114 may further react with the first treatment agent to form a second or additional treatment agent.

For example, a wipe 100 may carry a chemical compound, such as Sodium percarbonate in dry form, and a cooperating substance 114 may include glycolic or acetic acid in liquid form. Excess water in the substance 114 may react with the Sodium percarbonate to form Hydrogen peroxide, and the acetic or glycolic acid portion of compound 114 may then react with a portion of the Hydrogen peroxide to form peracetic acid. In a case where Hydrogen peroxide is carried in dry form (such as adsorbed into a high surface area material to form an essentially dry or dry-feeling powder, granule, pellet, bead, brick, or cake material), water in compound 114 may preferentially displace the Hydrogen peroxide to act as a first treatment agent, and if present, acetic or glycolic acid in compound 114 can also interact with the Hydrogen peroxide to form peracetic acid as a second treatment agent. It is within contemplation that compound 114 can sometimes be or include tap water.

In certain other embodiments within contemplation, a fluid source may include two or more chemical compounds that are separately stored, but when sprayed together onto a wipe (or directly onto a surface), generate a biocidal substance effective to disinfect and/or sterilize a surface. In that case, an operable wipe 100 may be embodied as a commercially available paper towel, or the like. An operable fluid source includes a pair of spray bottles 116 (e.g., FIG. 2), or a single spray bottle having two or more containers with provision to dispense two or more chemical compounds simultaneously. A multi-compartment fluid source may be included in a wipe holder, or simply used in conjunction with a disposable wipe 100.

For one example, one container may hold Sodium chlorite and another container may hold Citric acid. When sprayed together onto a wipe 108, Chlorine dioxide is created on the wipe 108, which can then be used to sterilize or disinfect a surface. A further non-limiting example includes a fluid source with one container holding Iron catalyst in solution and Hydrogen peroxide in another container. When sprayed together onto a wipe (or even directly onto a surface), the Fenton reaction generates Hydroxyl radicals to disinfect or sterilize the surface. In another embodiment, a spray bottle with either one compartment or multiple compartments can generate a sterilizing agent from just one chemical or multiple chemicals in different compartments to generate sterilizing agent on demand to sterilize, or otherwise treat, a surface.

Figure 13:
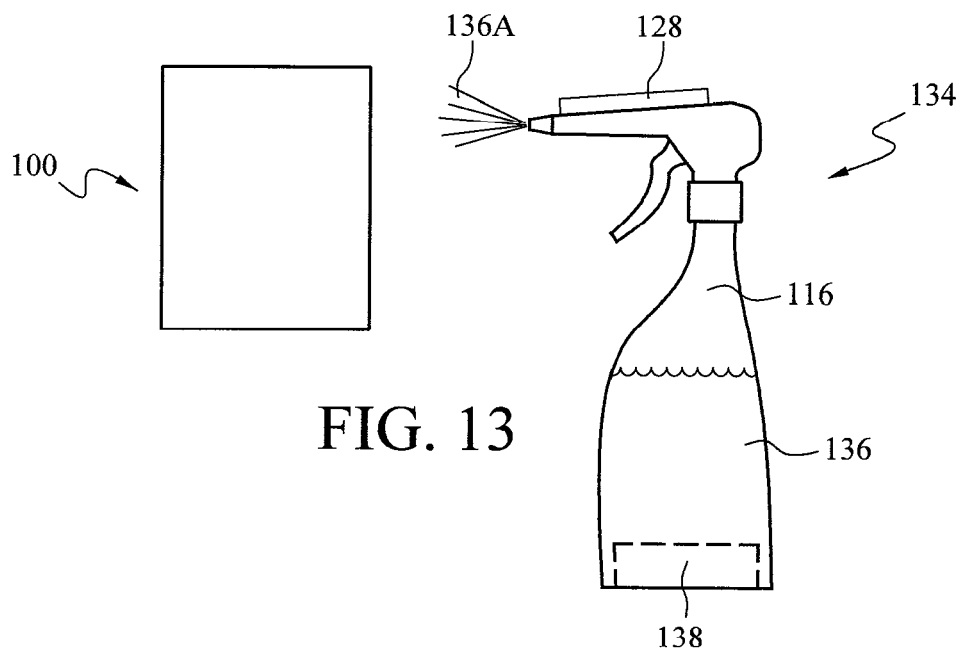
Figure 14:
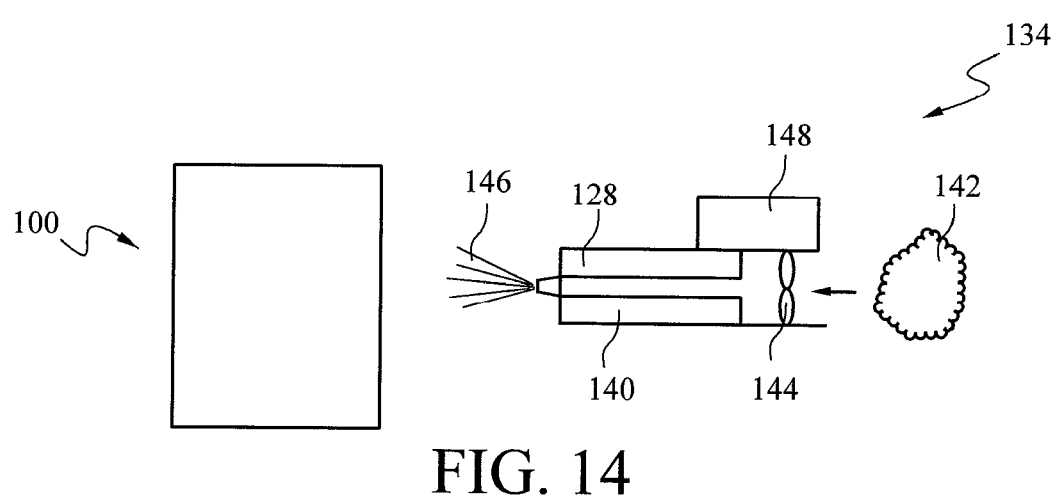
FIG. 14 is a pictorial view in elevation of a disposable wipe in combination with an alternative workable generator of Hydroxyl radicals.

FIGS. 13 and 14 illustrate alternative embodiments, generally 134, that generate a toxic, biocidal, or sterilizing agent on demand Versions of these embodiments may also include a wipe holder, be incorporated into a wipe holder, or may otherwise be employed in combination with one or more disposable wipe 100. FIG. 13 illustrates a spray bottle 116 adapted to carry a UV light 128 for irradiating a stream of fluid 136 to permit discharge of irradiated fluid 136A to dispose one or more treatment agent on a wipe 100. UV light 128 may conveniently be powered by an on-board power source, such as battery 138, for untethered operation. Other times, UV light 128 may be powered by a conventional cord-and-electric-outlet arrangement. Workable fluids 136 include Hydrogen peroxide ($H_2O_2$) and/or an Alkali-perchlorate solution.

FIG. 14 illustrates another embodiment 134 in which UV light 128 is arranged to impinge onto a treatment agent precursor 140, such as Alkali-percarbonate. Moisture 142 is urged by a device (such as a fan 144, pump, or other device), to flow through the irradiated zone, and produce a treatment agent 146 that is applied to the treatment wipe 100. Elements of a device such as the device 134 in FIG. 14 may be operated, at least in part, by a control module 148. Control module 148 may include an on-board power source, or communicate to a power source.

Figure 15:
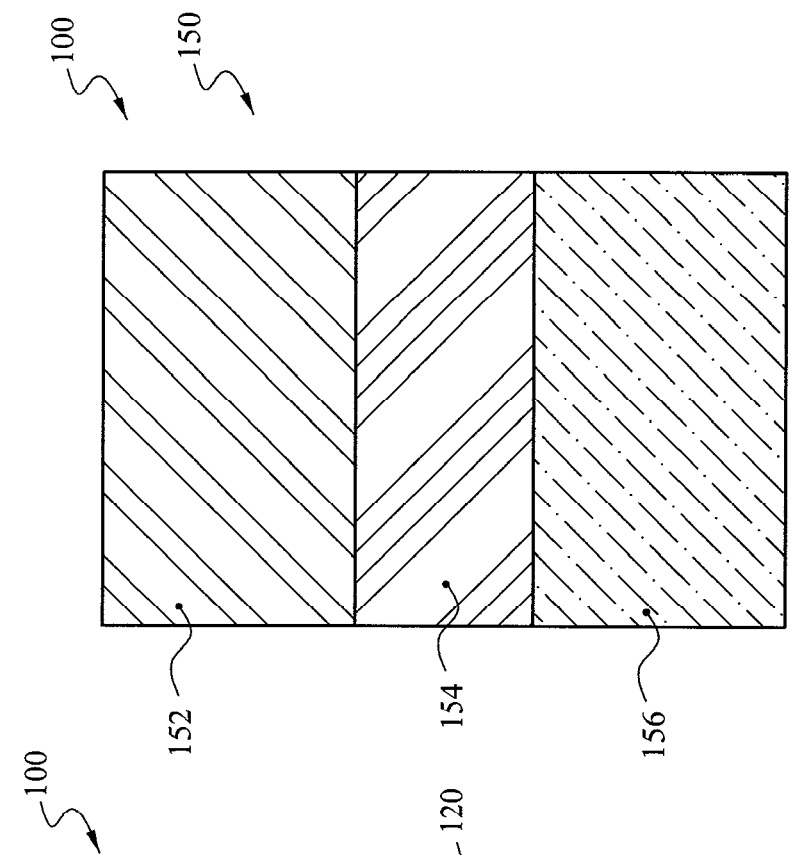
FIG. 15 is a pictorial view of a multi-compartment embodiment of a wipe.

FIG. 15 illustrates a multi-compartment embodiment 150 of a treatment wipe 100, which can be used separately, or in combination with a wipe holder 120. Multi-compartment wipe 150 includes a first compartment 152, second compartment 154, and third compartment 156. A compartment may be defined by dividing walls, or even sometimes by a space disposed between quantities of chemical compounds or electrodes that may be carried in various ways on a wipe 100. In one preferred embodiment 150, compartment 152 carries an Alkali-percarbonate; compartment 154 carries Citric acid; and compartment 156 carries Iron Sulfate ($FeSO_4$).

Figure 16:
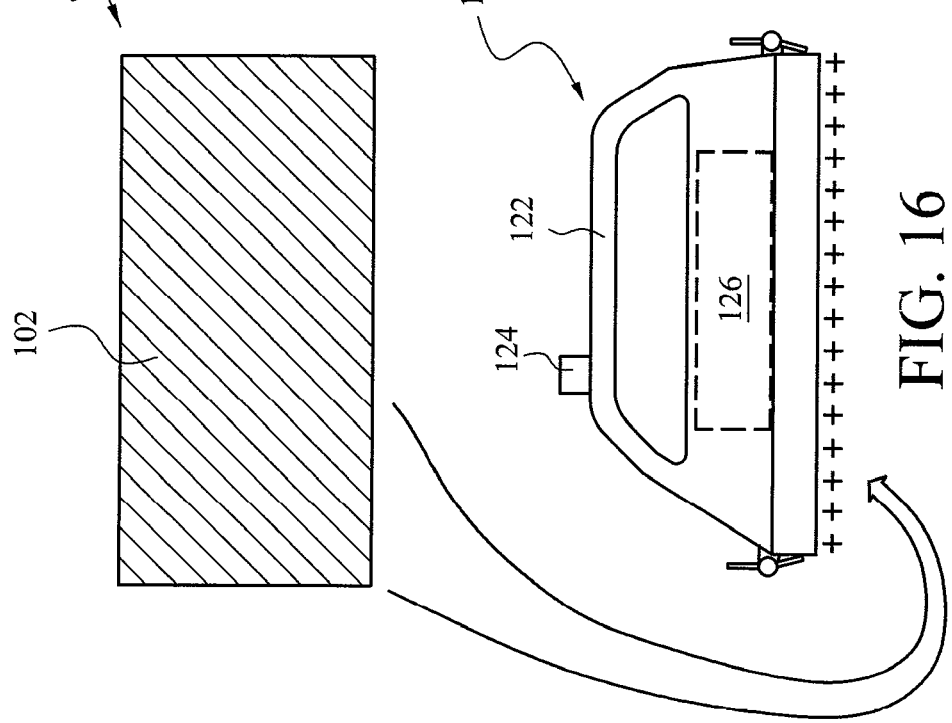
FIG. 16 is a pictorial view of another embodiment including a holder and wipe that incorporates a positive charge dispenser.

FIG. 16 shows another embodiment including a wipe holder 120 and wipe 100, wherein the wipe holder 120 operates as a positive charge dispenser. The wipe 100 illustrated in FIG. 16 includes a biocidal carrying electrode 102 that is activated by the wipe holder 120. The wipe holder 120 illustrated in FIG. 16 can put a positive charge on the wipe to attract gram negative bacteria and microbes. Certain embodiments may be structured such that, subsequently, or alternatively, or even simultaneously, holder 120 may induce a negative charge on the wipe to attract gram positive bacteria or microbes. Once the bacteria or microbes are attracted and contact the wipe, a biocidal agent included in the conductive electrode 102 kills all the bacteria or microbes.

Figure 17:
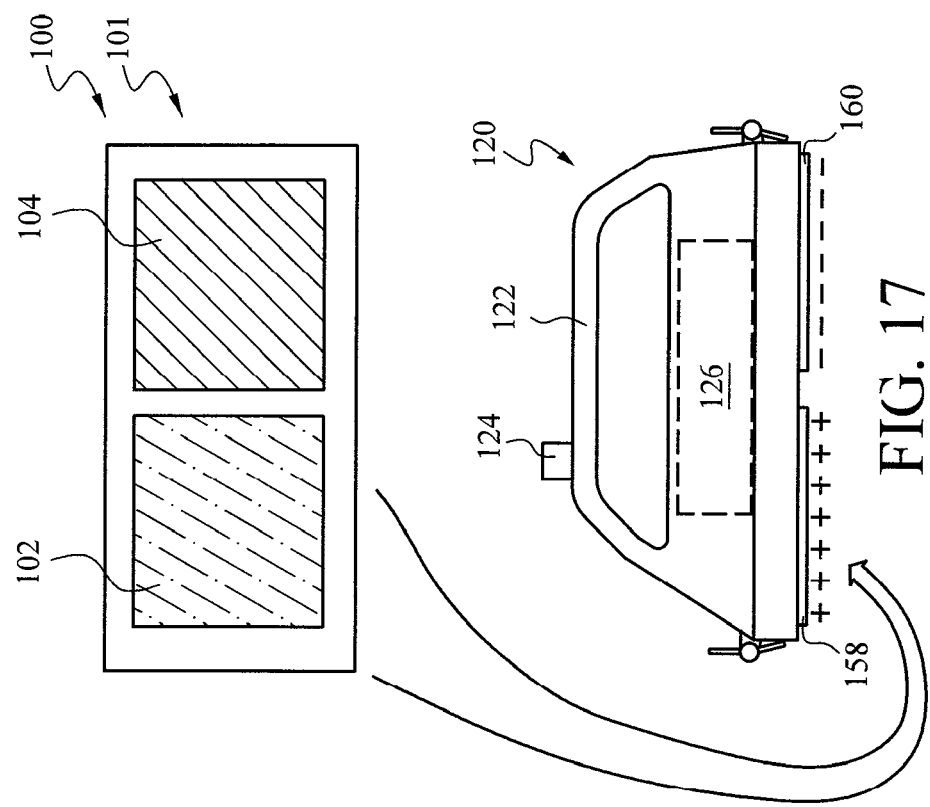
FIG. 17 is a pictorial view of another embodiment including a holder and wipe that incorporates a dual charge dispenser.

FIG. 17 illustrates an embodiment of a wipe holder 120 including both of a positive electrode 158 and a negative electrode 160 to simultaneously apply positive and negative charge to different areas of a wipe 100. The electrodes 102 and 104 of two-electrode wipe 101 in FIG. 17 are electrically conductive, and desirably each includes one or more biocidal agent.

Figure 18:
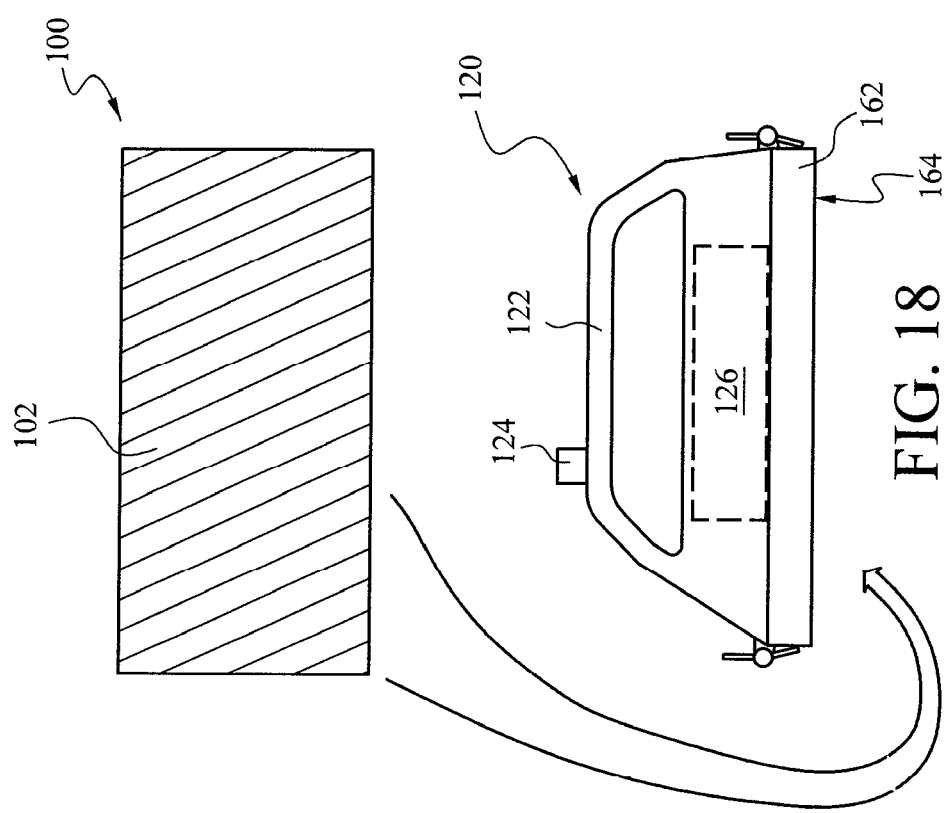
FIG. 18 is a pictorial view of another embodiment including a holder and various wipes that incorporate a thermal element.

FIG. 18 illustrates still another embodiment of a wipe holder 120 and a wipe 100, wherein the wipe holder 120 includes a thermal heating element 162. Desirably, the thermally conductive surface 164 is capable of attaining over 100 degrees Centigrade. A cooperating electrode, such as electrode 102, may include Sodium Chlorite trihydrate, or Sodium Chlorite trihydrate embedded into, or otherwise carried on the wipe 100.

Figure 19:
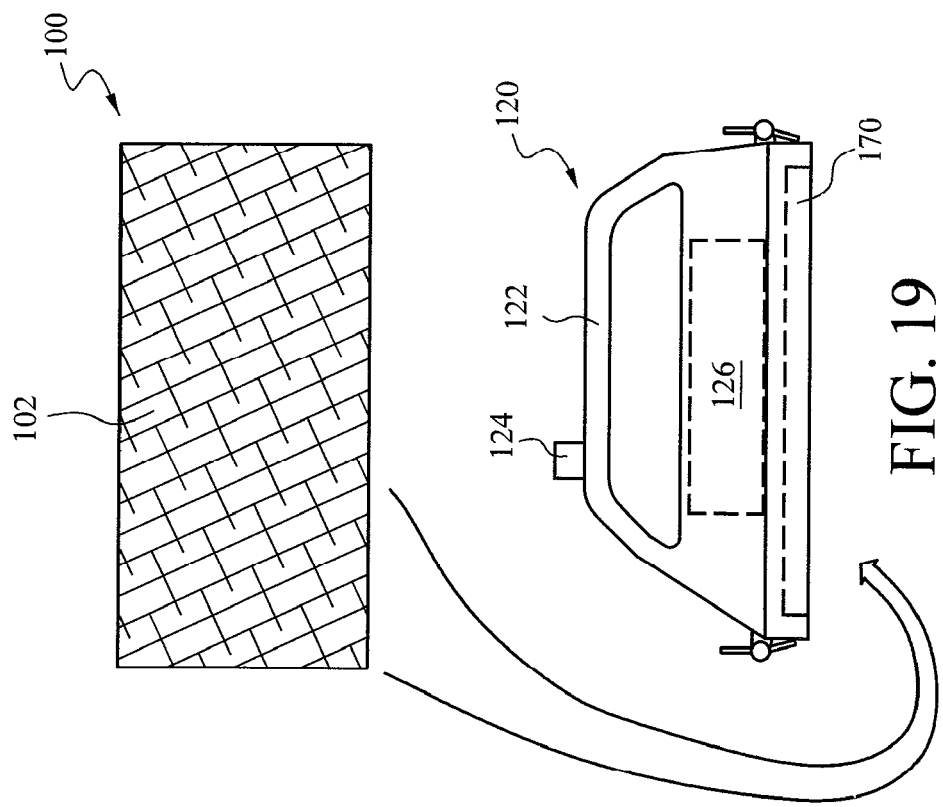
FIG. 19 is a pictorial view of still another embodiment including a holder that incorporates a UV element and a cooperating wipe.

FIG. 19 shows another embodiment including a wipe holder 120 that incorporates a UV lamp element 170 with a cooperating wipe 100. In this arrangement, wipe 100 may carry one or more electrode 102 including Sodium Chlorite. Further, sometimes a catalyst, such as nano-Titanium Oxide ($TiO_2$) or nano-Galium Nitride (GaN) needles, tubes, wires, and the like may also be included to enhance formation of one or more treatment agent(s).

Disposable wipes 100, such as single-electrode wipe 101, or a multi-electrode wipe such as 108 or 150, can be manufactured in a reel-to-reel process. Electrodes, or separate chemical compound elements, may be applied to discrete body portions with a painting-type, or printing-type process as a ribbon of body material passes by. Individual wipes may then be sectioned from the ribbon, stacked, and packaged, as desired.

Figure 20:
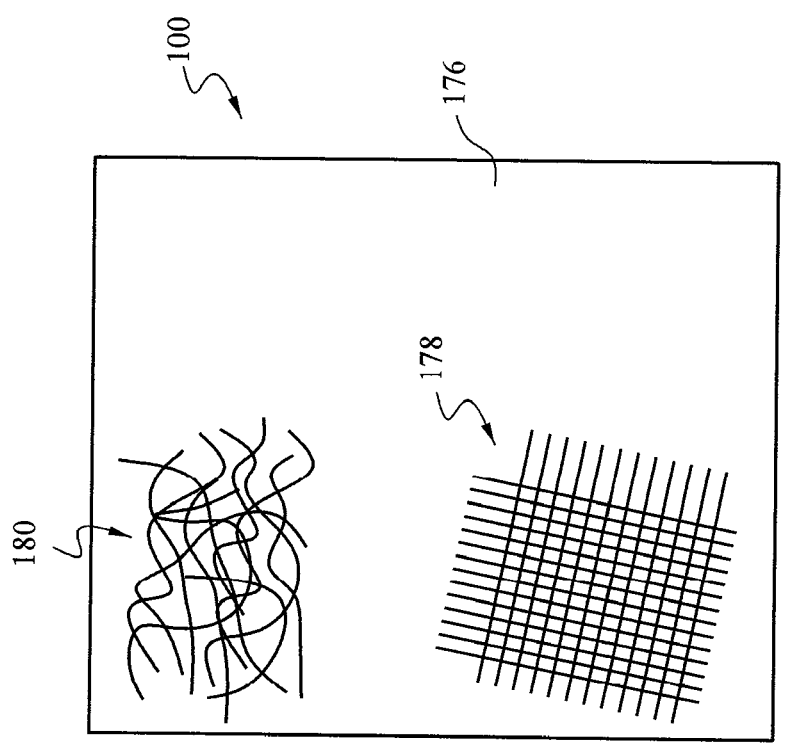
FIG. 20 is a pictorial plan view of another embodiment of a wipe.
Figure 21:
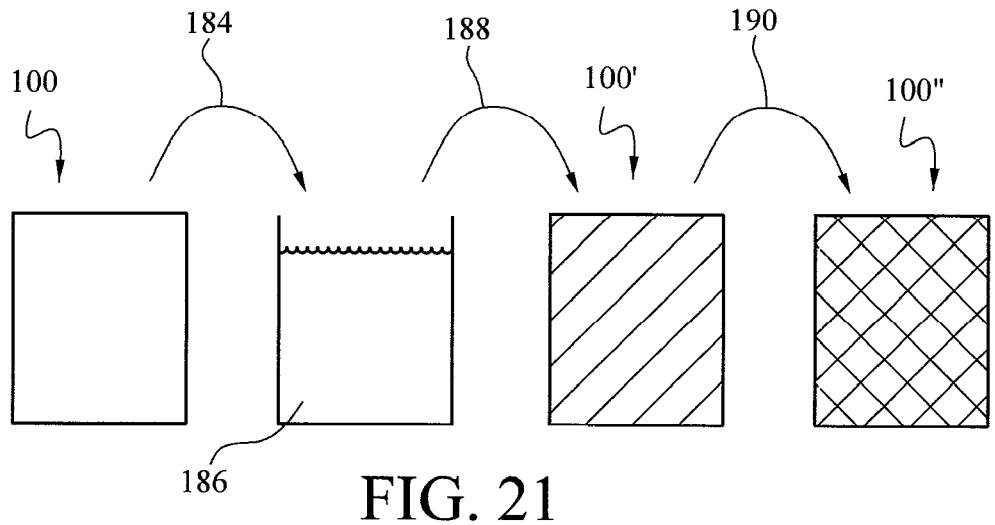
FIG. 21 is a pictorial side view of a workable manufacturing process to make a wipe similar to that illustrated in FIG. 20.

With reference to FIGS. 20 and 21, an alternative embodiment of a disposable treatment wipe can be constructed to generate alcohol when activated by water. With reference to FIG. 20, a treatment wipe 100 of this type provides a framework on which is carried a compound 176 that generates an active cleaning, sterilizing, or deodorizing agent when combined with a second element, such as water or other solvent. A suitable framework can be formed by warp and weave fibers in a woven cloth, generally 178, or random strands, generally 180, arranged to form a membrane or pad, as well as many other substrates that can carry a workable alcohol-producing compound. A workable compound 176 includes a form of dextrin combined with an alcohol to form a substantially dry and solid material.

As with previously-described wipes, the treatment wipe embodiment 100 illustrated in FIG. 20 may be used alone, or in combination with a wipe holder of some sort. It is within contemplation that an embodiment such as illustrated in FIG. 20 may also be used in combination with one or more other type of disposable (or even non-disposable) wipe structured as previously described. Nothing in this description is intended to be limiting.

A solid alcohol treatment wipe 100 of the type illustrated in FIG. 20 may be manufactured in a variety of ways. One workable way includes incorporating a dextrin compound, such as maltodextrin or cyclodextrin, and an alcohol, such as ethyl alcohol, as a composite in the wipe 100. As illustrated, a wipe 100 can be submerged (as indicated by arrow 184) into a solution of a (modifier)dextrin compound 186 or otherwise sufficiently wetted with the solution, removed and dried (as indicated by arrow 188), to form a wipe 100' having (modifier)dextrin (dry) embedded onto the wipe 100'. An alcohol solution is then dispersed (e.g. sprayed) onto the wipe (as indicated by arrow 190) and forms a (modifier) dextrin-Alcohol complex in-situ on the wipe 100". The wipe 100" is then dried (if needed), and can be stored, packaged, etc., prior to use. In use, a fluid such as water may be sprayed onto the wipe 100", or the surface to be cleaned, deodorized, sanitized, disinfected, and/or sterilized, and the compound 176 carried on the treatment wipe 100" combines with that fluid to generate alcohol for use as a treatment agent.

An alternative embodiment may be manufactured by wetting the wipe substrate (e.g., dipping) in a Sodium Carbonate solution, then drying the impregnated wipe. Subsequently, the wipe can be sprayed, or again appropriately wetted, with a solution of stable Hydrogen Peroxide containing Silver nitrate or Silver Citrate or Benzyl alcohol, or Triclosan, and then dried. Upon activation by fluid, such as water, the resulting wipe will generate and deliver disinfectants to an object to be treated and kill microbes on its surface.

Another embodiment within contemplation may be manufactured by wetting a wipe substrate with a concentrated solution of Sodium Carbonate and Magnesium Sulfate, then drying the wipe. Subsequently, a highly concentrated solution of Hydrogen Peroxide containing Silver nitrate can be sprayed or otherwise applied to the wipe. Then the wipe is again dried. Upon activation by a fluid, such as water, the wipe delivers a disinfectant to the surface to be treated.

Figure 22:
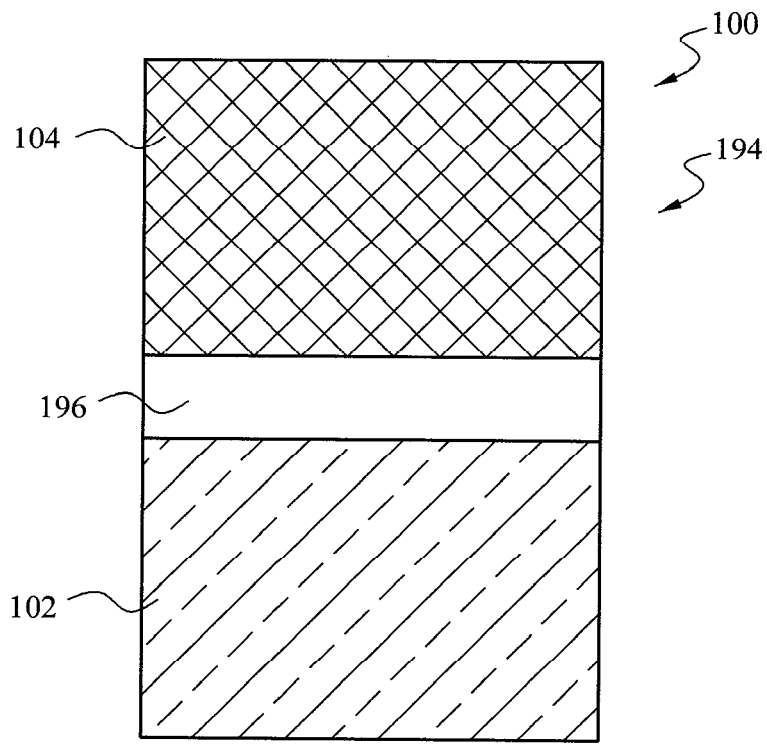
FIG. 22 is a pictorial view of an embodiment with an on-board charge generator.

Embodiments have been disclosed above in which one or more area of electrical charge is/are established by a wipe holder, or an external source of electrical charge. With reference now to FIG. 22, a treatment wipe 100 may be structured to include a battery to provide on-board capability to generate areas of positive and negative electrical charges. The charge-generating treatment wipe embodiment generally indicated at 194 includes first electrode 102 and second electrode 104. Desirably, those electrodes are separated by a divider 196. A workable divider 196 includes a space between compounds that make up the electrodes, or sometimes, a physical wall or barrier. In this case, electrode 102 may be regarded as the anode, and electrode 104 may be regarded as the cathode.

An exemplary anode 102 may include Zinc, a biocidal agent, and Sodium Chloride. An exemplary cooperating cathode 104 may include Silver Chloride, a biocidal agent, Sodium Chloride, and Carbon. Upon activation by a fluid, such as water, Zinc becomes the positive electrode while Silver Chloride becomes the negative electrode. The gram negative microbes will be attracted to the Zinc electrode, and the gram positive microbes will be attracted to the Silver Chloride electrode. Biocidal material contained in the respective electrodes will kill the attracted microbes, as well as be delivered to the surface to be treated. Workable anodes include Zinc, Aluminum, and Magnesium. Workable cathodes include Carbon and Silver Halides. Workable biocidal agents nonexclusively include quaternary ammonium compounds, Triclosan, or other organic biocidal agents.

Figure 23:
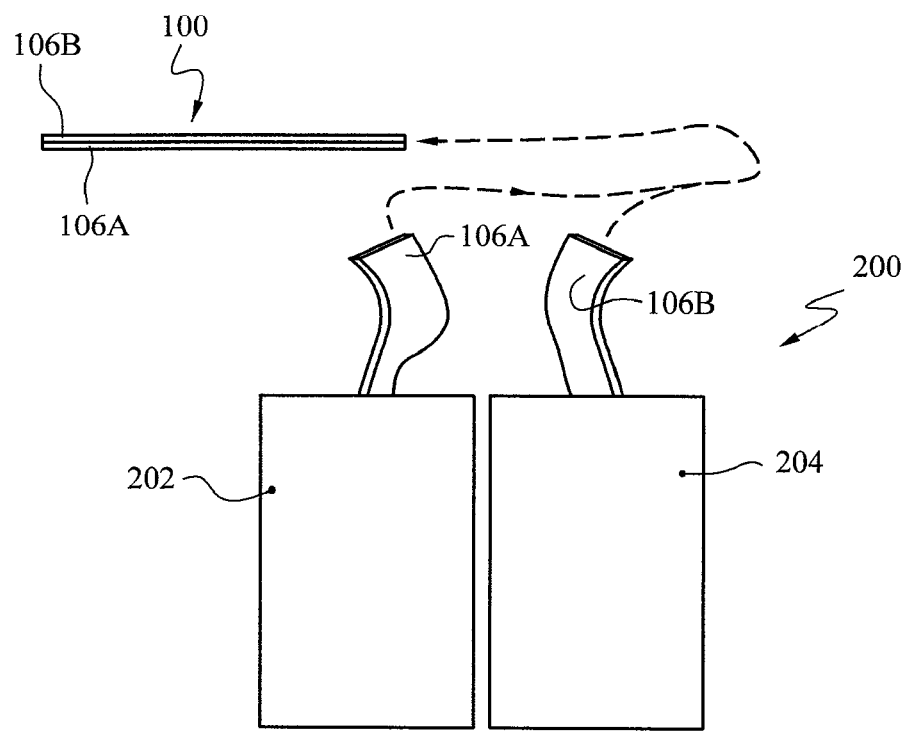
FIGS. 23 and 24 are pictorial views in elevation of wipe embodiments in association with wipe component dispensers.

A treatment wipe 100 may be formed by a combination of a plurality of prepared-in-advance substrates that may be dispensed, combined, and used at the location and time of treatment of an object. With reference to FIG. 23, wipe 100 is formed by combining a first substrate 106A with a cooperatingly structured second substrate 106B.

Figure 24:
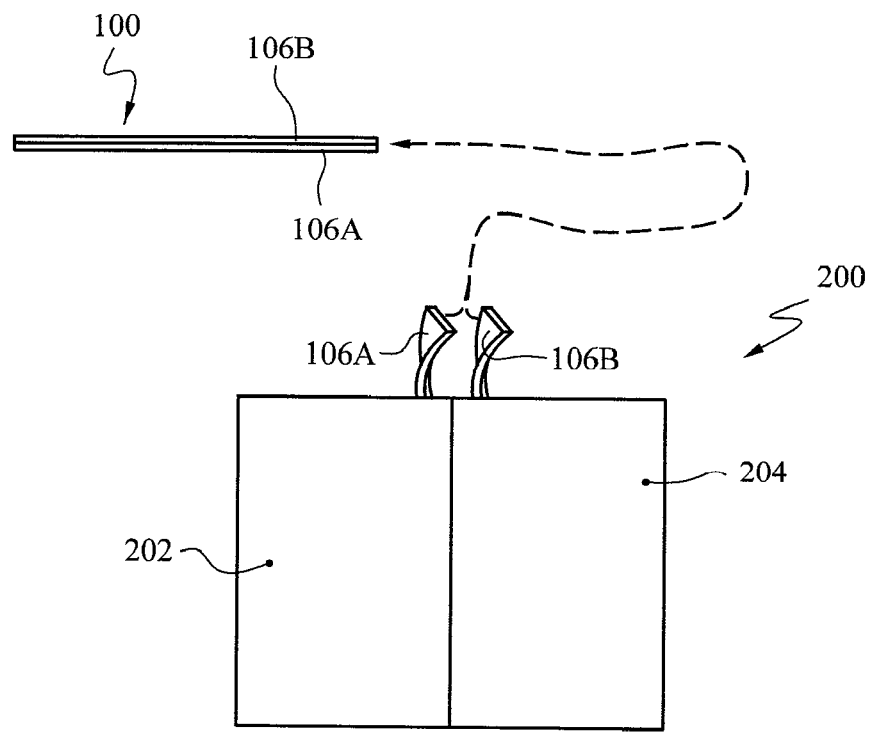

A convenient dispenser for cooperating substrates, generally 200, provides a first compartment or chamber 202 and a second compartment or chamber 204. Individual compartments may be separate elements, or, connected together in a unitary structure. The dispenser 200 in FIG. 24 is structured in such a way that substrates 106A and 106B are simultaneously dispensed and combined for use. Compartments desirably are each structured to contain a plurality of substrates. Sometimes substrates are stored in a dry, or near-dry condition. Other times, substrates may be moist or wet (damp). Therefore certain compartments 202, 204 are structured to confine moisture or even to hold excess or free-standing liquid.

In accordance with the foregoing disclosure, it should be realized that first compartment 202 may contain substrates 106A that individually carry one or more of: Hydrogen Peroxide, Sodium Chlorite, Sodium Chlorate, and/or Quaternary Ammonium salt. In further harmony with the above disclosure, second chamber 204 may confine substrates 106B that individually carry on or more of Silver nitrate, Silver Citrate, Citric acid (e.g. vinegar), glycolic acid, any mild acid, solid acid at room temperature or similar ambient conditions, and Iron Sulfate.

In one exemplary embodiment 200, chamber 202 holds a plurality of substrates 106A that carry Hydrogen Peroxide, and chamber 204 holds substrates 106B that carry Iron Sulfate solution. When combined, the compounds carried on the substrates form a wipe 100 that produces Hydroxyl radicals as a treatment agent that may be applied to an object to deodorize, disinfect, and/or sterilize the object.

In another currently preferred embodiment 200, chamber 202 holds a plurality of substrates 106A that carry Hydrogen Peroxide, and chamber 204 holds substrates 106B that carry an acid, such as Citric acid, or vinegar, or glycolic acid. Substrates 106A may include or be embodied as commercially available damp wipes that include Hydrogen Peroxide. Substrates 106B may be embodied as similar wipes that carry the acid element in either damp or dry form. It is currently preferred for both wipe substrates 106A and 106B to be stored in a damp state. When combined, the compounds carried on the pair of substrates form a wipe 100 that produces peracetic acid as a treatment agent that may be applied to an object to deodorize, disinfect, and/or sterilize the object.

Figure 25:
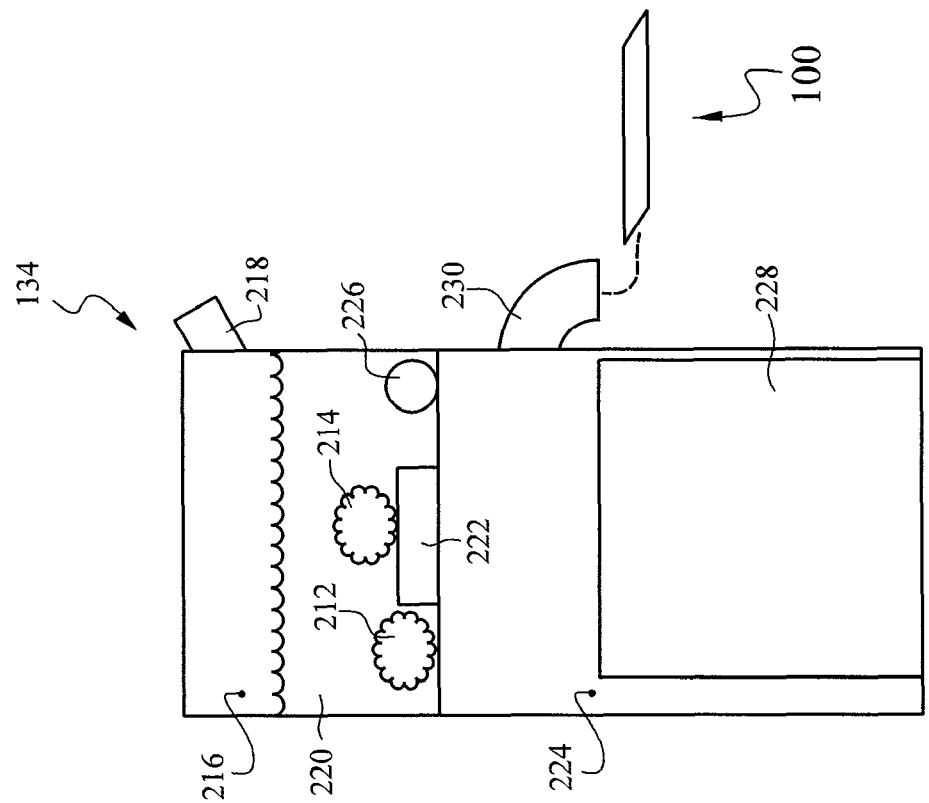
FIG. 25 is a first pictorial view in elevation of an applicator of treatment agent to a plurality of wipes.
Figure 26:
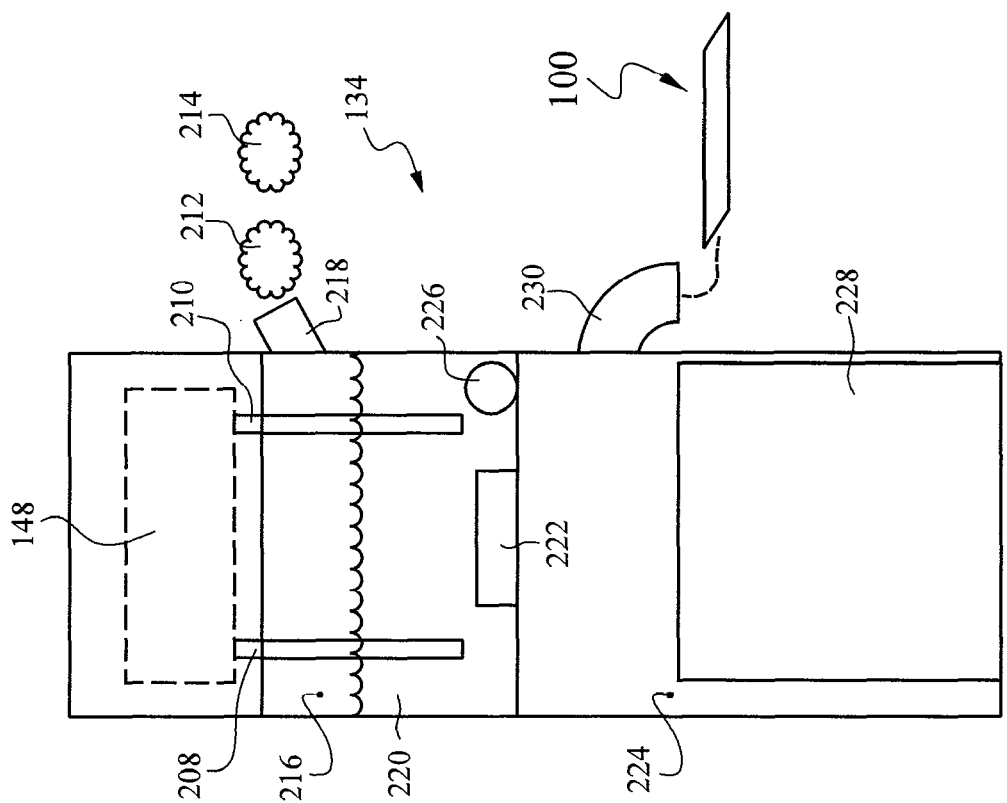
FIG. 26 is a second pictorial view in elevation of an applicator of treatment agent to a plurality of wipes.

Embodiments according to certain principles of the invention may be structured to generate one or more treatment agent on demand, and apply the product(s) to a wipe substrate or body 106. Some examples are illustrated in FIGS. 13 and 14. Additional such embodiments 134 are illustrated in FIGS. 25 and 26. In FIG. 25, treatment applicator 134 includes a first electrode 208 configured as a cathode. A second electrode 210 is configured as an anode. Precursor elements 212 and 214 (which may be salt and water, respectively), are added to upper chamber 216 through a sealable door 218. A control module 148 energizes the electrodes 208 and 210, to produce one or more treatment agent from precursor elements 212, 214. The device 134 may be embodied as a cordless, or corded appliance. Typically, the device 134 is sized on the scale of a 2-slice toaster. An advantage of the device 134 in FIG. 25 is that it may be transported and sold without requiring the additional weight of water, which is supplied buy a consumer at the location of wipe creation.

When the precursor elements include salt and water, the device 134 produces a treatment solution 220 including Sodium hypochlorite. That solution may be applied through a re-sealable aperture 222 to a plurality of wipe bodies 106 that are stored in lower compartment or chamber 224. A re-sealable aperture 222 may be embodied in many forms, including a guillotine valve, for example. Sometimes a stabilizer 226 may be included in the treatment solution. A door or opening 228 permits adding dry wipe bodies 106 to chamber 224. Desirably, a mechanism is provided to facilitate removal of a desired number of prepared wipes 100. One such device includes wipe dispensing spout or chute 230. It is within contemplation that chamber 216 may communicate through a metering device to dispense an appropriate amount of treatment fluid to one or more wipe 100 at a time.

The treatment agent applicator 134 illustrated in FIG. 26 is similar in certain respects to the embodiment in FIG. 25, and is numbered accordingly. Applicator 134 in FIG. 26 is particularly structured to permit chemical reaction of a plurality of precursor compounds (e.g. 212, 214) to generate Hydroxyl radicals in top chamber 216 upon addition of water to react with compounds 212, 214. Compounds 212, 214 may be selected from couples disclosed above, and include Sodium percarbonate and Silver Nitrate; Magnesium Sulfate and Iron sulfate; Sodium percarbonate and ozone generator; Sodium percarbonate and UV light; catalyst and UV light; Hydrogen peroxide and Iron Sulfate or UV light or ozone generator.

The embodiment 134 in FIG. 26 may alternatively be operated to generate disinfecting chemicals or treatment agents. Operable couples in that case nonexclusively include: Silver halides and UV light; Silver citrate and citric acid; Sodium chlorate or Sodium chlorite and citric acid or other mild acid; Quaternary Ammonium salt, with or without Silver halides or citrates or Nitrates; and Ozone generator.

EXEMPLARY TEST DATA

A wipe was made by printing two carbon electrodes onto a substrate, which was then saturated with Sodium Chloride. A prototype wipe holder with a battery powered the electrodes to form Sodium Hypochlorite as a treatment agent. Test data for treatment of a stainless steel surface on a coupon contaminated with *E. coli* resulted from following the protocols set forth below:

Application Method 1=2 squirts of tap water on coupon surface, 2 squirts on prototype pad, turn on prototype for 20 sec, wipe surface 3 times, allow sample to sit for 10 min, and analyze sample.

Application Method 2=2 squirts of tap water on coupon surface, 3 squirts on prototype pad, turn on prototype for 30 sec, wipe surface 4 times, allow sample to sit for 10 min, and analyze sample.

In either case, the percent reduction of *E. coli* ACC 8739 was >99.981 percent.

With reference now to FIGS. 27 and 28, a holder 120 for a wipe may be embodied as a mitt, mitten, or glove 240. Mitt 240 constitutes a housing that provides conventional enveloping structure into which a user's hand may be inserted to manipulate the mitt during deodorizing, disinfecting, and/or sterilizing a surface. Other workable housings and alternative structures may be envisioned to provide structure arranged to receive a human hand to manipulate a holder 120 during deodorizing, disinfecting, and/or sterilizing a surface.

The housing provided by illustrated mitt 240 carries a plurality of energizing transducers, generally 242. Energizing transducers 242 associated with a housing or holder may all be the same, or they may include an assortment of different transducers. A workable transducer 242 is operable to modify a treatment agent, or to create a treatment agent, or sometimes, both. Workable energizing transducers 242 nonexclusively include: electrical field such as cold plasma generator, UV light, ion generator, and fluid particle size-modifying. A plurality of cold plasma generating transducers 244 are particularly illustrated in e.g., FIG. 27.

Desirably, a fluid particle size-modifying transducer is operable to create micro-, micron-, or nano-sized particles of a treatment agent. A particle size-modifying transducer, or nebulizer, may be embodied in various forms, including ultrasonic, electrical (e.g., piezo), mechanical, such as on a pressurized fluid source (e.g., fluid atomizer with a large pressure differential across a small aperture and a strong spin being imparted to the exiting fluid), and thermal fogger.

It is typically desirable to provide a portable power source (e.g., a battery pack and control system 246) in operable association with a wipe holder, such as the mitt 240, to facilitate deodorizing, disinfecting, and/or sterilizing a surface with the device. Wires or control leads, generally 248, permit placement of the power/control system 246 at a convenient location. Exemplary convenient locations include the back of a mitt 240, or on the belt of an operator. A heavier battery pack may be carried in a backpack worn by an operator, or even placed on the floor in the vicinity of an object to be treated. However, it is within contemplation that a wipe holder 120 may also be structured for tethered operation to a conventional plug-in electrical outlet.

With reference to FIG. 28, mitt 240 constitutes an element of an applicator of energized treatment agent, generally indicated at 250. By "energized" it is intended to mean that the applicator 250 is structured to apply a modified and energized form of a treatment agent, or an alternative energized treatment agent derived from or made from an original treatment agent, which energized form has an enhanced power to kill microbes, when compared to the original treatment agent.

The applicator 250 illustrated in FIG. 28 includes a holder 120 (the mitt 240) and a wipe 100. Illustrated wipe 100 is structured as an over-mitt 252, inside of which mitt 240 can be inserted. Over-mitt 252 may be installed in operable position in registration with a holder 240 like a sock onto a foot or a mitten onto a hand. A wipe operable with a holder 240 may be embodied in alternative shapes, nonexclusively including a rectangular bag or open-ended cylinder. Wipe 252 may be structured as a disposable membrane-like element according to previously described wipes. However, a preferred wipe 252 carries a fluidized treatment agent, such as Hydrogen peroxide in a range of about 2% to about 30%.

In certain embodiments, such as when over-mitt 252 carries a fluidized treatment agent, for example Hydrogen Peroxide, and a transducer 242 is embodied as a nebulizer to convert the Hydrogen Peroxide into micron- or nano-sized particles, the system illustrated in FIG. 28 applies energized treatment agent as a fog onto a treatment site or surface, and the energized treatment agent is wiped by the over-mitt 252. Sometimes, a plain wipe 100 (e.g., a dry paper towel, or cloth) may also be used, in combination with an embodiment such as illustrated in FIG. 28 and particularly described here, to remove residual treatment agent from the surface.

A preferred mitt 240 provides a holder 120 for a wipe 100 (see FIGS. 27 and 28) that is compliant and permits application to, and contact of a wipe 100 with, an irregular, non-flat, or curved surface. A user's hand may deform the wipe 100 to cause a desired conformation of a disposable wipe 100 to the surface to be treated.

A mitt 240 may be structured to be reusable. An exterior surface 254 may be treated, e.g., rubberized, to permit cleaning the mitt for reuse with a plurality of successive disposable wipes 100.

Figure 29:
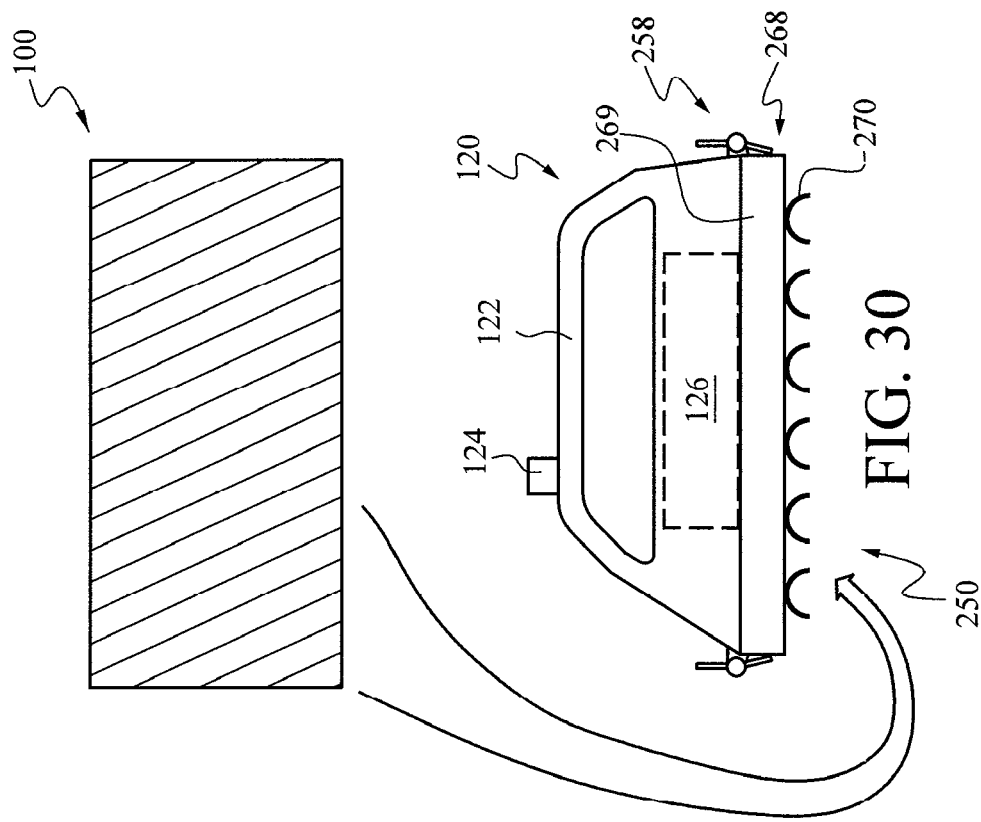
FIG. 29 is a pictorial view of another embodiment, generally illustrating one or more energizing transducers associated with a holder, and particularly illustrating an energizing transducer adapted to generate a cold plasma.

FIG. 29 illustrates a wipe 100 in combination with a holder 120 that is particularly structured to impart cold plasma to the wipe. The wipe 100 may be associated with the holder 120 by affixing opposite ends of the wipe 100 to clamps 258. Wipe holder 120 in FIG. 29 includes a cold plasma generator/transducer 244, arranged to impart plasma to a wipe 100 at a wipe-support surface 262. The embodiment 250 in FIG. 29 may be regarded as a fairly rigid embodiment, although a compliant surface 262 is within contemplation in alternative embodiments. The plasma generator 244 transforms and "energizes" a portion of a treatment agent, such as Hydrogen Peroxide carried on a wipe 100, into Hydroxyl radicals, thereby energizing the treatment agent.

Various types of cold plasma generators 244 may be employed in embodiments of the invention. Operable cold plasma transducers of various types including Dielectric barrier discharges (DBD), resistive barrier discharges (RBD), cascaded dielectric barrier discharge (CDBD), corona plasma discharges (CPD), and the Atmospheric Pressure Plasma Jet (APPJ) or the plasma plume, are disclosed in "Plasma Based Sterilization: Overview and the Stepwise Inactivation Process of Microbial by Non-thermal Atmospheric Pressure Plasma Jet", by M. R. Pervez, A. Begum, and M Laroussi, in the International Journal of Engineering & Technology IJET-IJENS Vol: 14 No: 05. The disclosure set forth in this paper is incorporated by this reference, as though set forth herein in its entirety.

An analysis of Surface Micro-Discharge plasma effect on microorganisms is presented in the Dissertation titled SURFACE MICRO-DISCHARGE (SMD)—ANALYSIS OF THE ANTIMICROBIAL EFFECT AND THE PLASMA CHEMISTRY, by Jin Jeon, geboren am 27 Sep. 1984 in Seoul/Südkorea. A similar analysis is set forth in "Cold Atmospheric Air Plasma Sterilization against Spores and Other Microorganisms of Clinical Interest", by Tobias G. Klämpfl, Georg Isbary, Tetsuji Shimizu, Yang-Fang Li, Julia L. Zimmermann, Wilhelm Stolz, Jürgen Schlegel, Gregor E. Morfill, and Hans-Ulrich Schmidt, in Appl Environ Microbiol., 2012 August; 78(15): 5077-5082. The disclosures set forth in these papers are also incorporated by this reference, as though set forth herein in their entirety.

Disinfection Testing of Commercially Available $H_2O_2$ Wipes

Procedure: *Geobacillus stearothermophilus* spores were procured from Croostex®. Tryptic Soy Broth was prepared in the lab as the growth media. The *Geobacillus* spores had a population of $1.5 \times 10^6$. Positive and negative controls were prepared to observe the growth and for comparison. The test procedure was as follows:

1. Place the spore plate on a clean and sterile surface facing upwards
2. Place the disinfecting wipe on top such that it contacts the spores
3. Wait for a specific time limit and then remove the wipe
4. Pick the spore plate and drop it into the media tube and place in the incubator The positive control was not treated with any disinfecting medium. Two positive controls were prepared, one with no treatment at all and one which was kept in contact with a wet wipe containing only water. In addition to the hydrogen peroxide wipe the spores were treated with a combination of the wipe and Cold Corona Plasma for 1 min, 30 sec and 15 sec. The negative control was prepared by treating the spore plate with 10% bleach for the same time as the wipe.

The treated spore plates were submerged into the media in test tubes which were then placed in an incubator shaker at 55° C. and 250 rpm. Test results are presented in Table 1. $H_2O_2$

TABLE 1

| Description | Time | % kill | Time | % kill | Time | % kill |
| --- | --- | --- | --- | --- | --- | --- |
| 3% $H_2O_2$ Wipe | 15 sec | 2% | 30 sec | 7% | 1 min | 24% |
| 3% $H_2O_2$ Wipe with Cold Corona Plasma | 15 sec | 27% | 30 sec | 56% | 1 min | 100% |

It can be observed that the exposure time increased the % kill for the hydrogen peroxide wipe. However, at 15 sec the % kill was quite low for the wipe. On combining the wipe with plasma, the potency of the wipe was increased as observed by the increase in the % kill. These experiments were conducted as a proof of concept to show that cold corona plasma can increase the potency of hydrogen peroxide.

Figure 30:
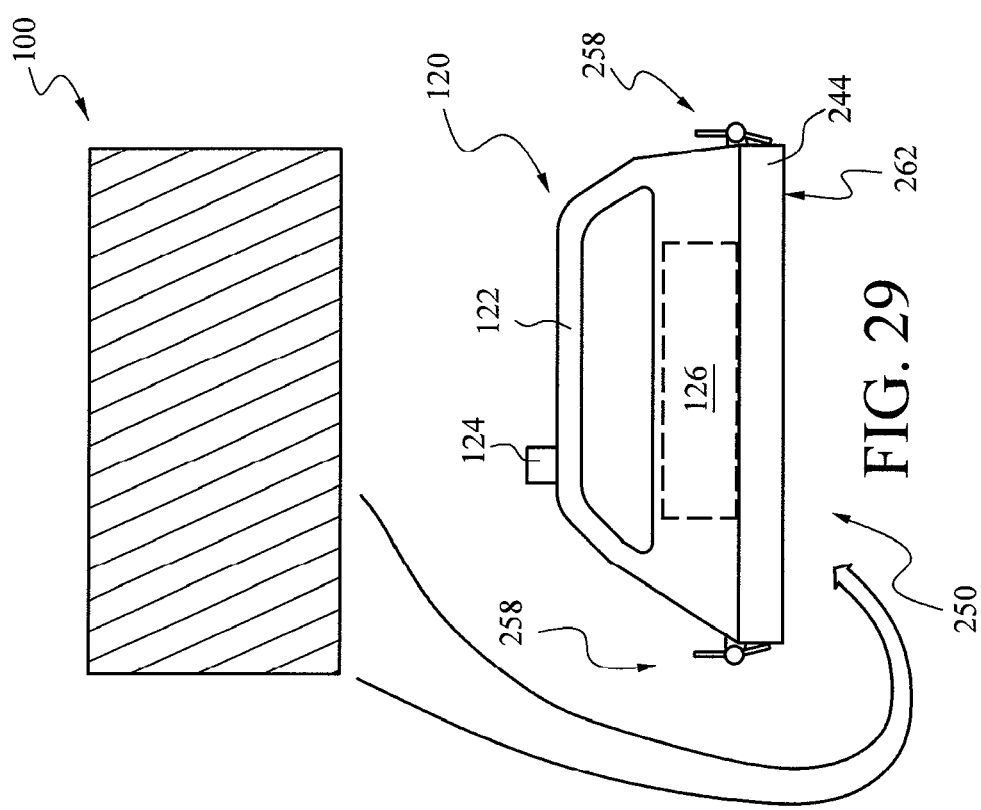
FIG. 30 is a pictorial view of another embodiment, having an energizing transducer adapted to modify particulate size of treatment agent that is applied to a surface.

FIG. 30 illustrates an embodiment having a nebulizer transducer, generally 268, such as an ultrasonic transducer 269, arranged to interact with an installed wipe 100. In the embodiment illustrated in FIG. 30, a plurality of optional brush elements 270 constitutes compliant ultrasonic extension elements that provide a degree of conformation of an installed wipe 100 to an irregular surface. A variety of nebulizing transducers are workable, including piezo, mechanical, and atomizing. A less preferred nebulizer includes a heat-activated nebulizer.

In certain embodiments, such as when a wipe 100 carries a fluidized chemical treatment agent, for examples Hydrogen Peroxide or peracetic acid, and a transducer 268 is embodied as a nebulizer to convert the Hydrogen Peroxide or peracetic acid into micron- or nano-sized particles, the system 250 illustrated in FIG. 30 acts as an applicator of energized treatment agent to apply energized treatment agent as a localized fog onto a treatment site or surface, and the energized treatment agent is wiped by an installed disposable wipe 100. Sometimes, an independently operated plain wipe 100 (i.e., dry) may also be used, in combination with an embodiment such as illustrated in FIG. 30 and particularly described here, to remove residual treatment agent from the surface.

Figure 31:
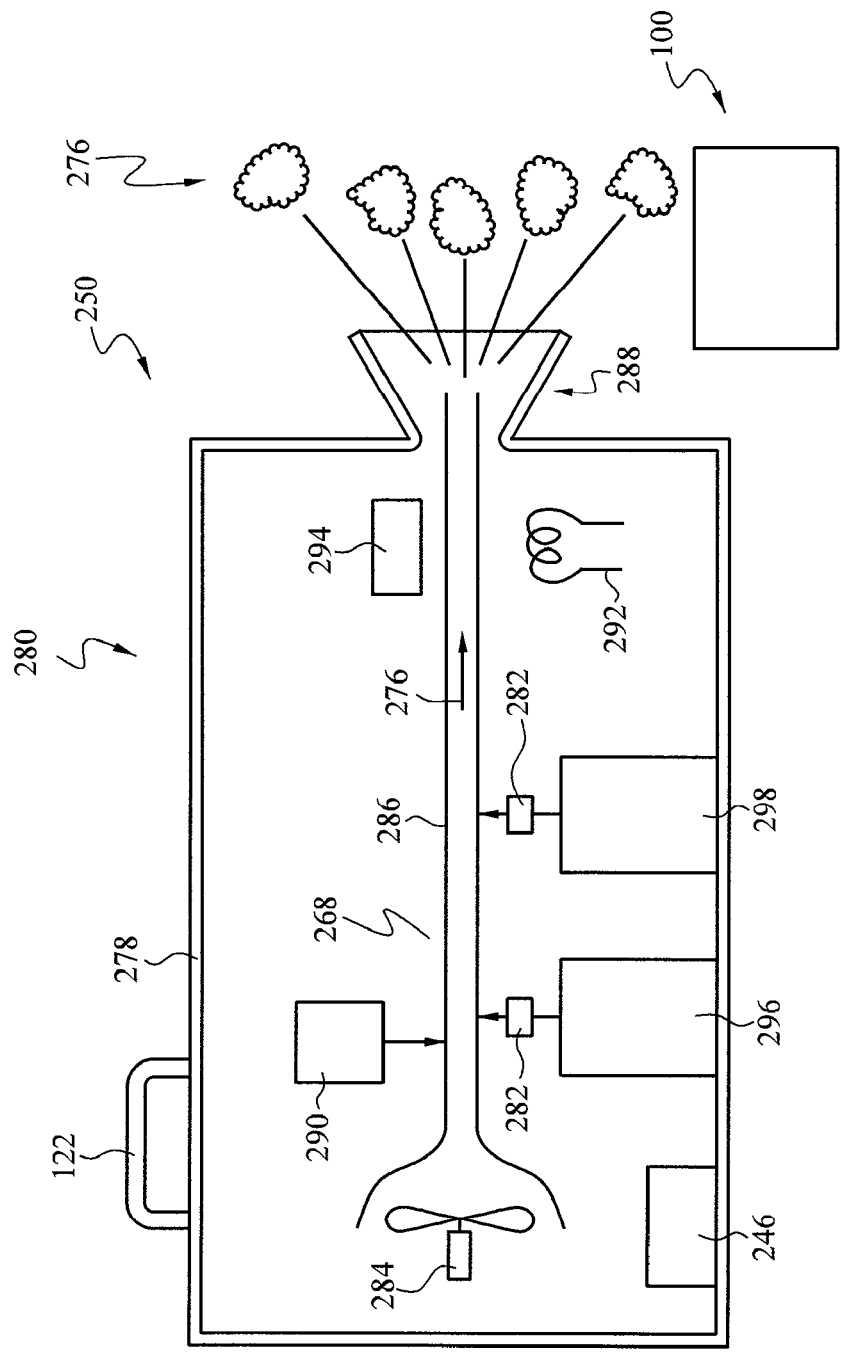
FIG. 31 is a side view of an applicator of treatment agent in combination with a wipe.

FIG. 31 illustrates another embodiment 250 of an applicator of energized treatment agent, generally 276. The embodiment 250 in FIG. 31 includes a housing 278 that may be associated with any of a plurality of energizing elements. As illustrated, housing 278 has a handle 122, which is structured to receive a human hand for manipulation of the housing 278 to deodorize, disinfect, and/or sterilize a treatment site. A preferred housing 278 is adapted for portable use as a stand-alone applicator, generally 280, and includes a portable power/control system 246.

A stand-alone applicator, such as applicator 280, may be used to apply energized treatment agent 276 to a surface independent of a wipe 100. In that case, a wipe 100 may be used to spread the treatment agent, apply a scrubbing action, and/or to remove the treatment agent from the treated surface. Further, the wipe 100 may even be a plain wipe, lacking in treatment agent. An exemplary operable wipe 100 for use with a stand-alone applicator 280 includes a paper towel, cotton cloth, and the like.

Typically, a housing 278 of a stand-alone applicator 280 holds at least one transducer, generally 268, effective to modify the size of treatment agent particles to create a discharge of fog particles having micro- or nano-sizes. An exemplary energizing transducer 268 is a nebulizer 282. Operable particle size-modifying transducers 268 have been described above, in connection with other embodiments, and non-exclusively include ultrasonic and piezo-activated transducers. Thermally actuated nebulizers are less preferred.

In FIG. 31, a fan 284 is provided to urge movement of energized treatment agent 276 along a guide 286 for discharge through an exhaust port, generally 288. Typically, the discharged treatment agent 276 can be characterized as being in a fog-state.

As illustrated in FIG. 31, a housing 278 may hold a plurality of transducers 268, which can include a plurality of nebulizers 282, among other different or similar transducers and treatment-modifying elements. As illustrated, an ion generator 290 may be placed in operable association for inclusion of ions in the discharged fog. Sometimes, a germicidal lamp 292 may be disposed to act on treatment agent. An exemplary germicidal lamp may be a UV lamp, and is typically selected to have an output wavelength in the range between about 250 to about 350 nm. It is also within contemplation that a cold plasma generator 294 may be included in certain embodiments 280. Other transducers within contemplation include a fluid atomizer, and an Ozone generator.

Applicators of energized treatment agent 250 may be embodied to include more than one treatment agent for application of a compound mixture of treatment agents to a treatment site. For example, the stand-alone applicator 280 in FIG. 31 includes a first container 296 in which to hold a quantity of a first fluidized treatment agent, and a second container 298 in which to hold a quantity of a second fluidized treatment agent. A preferred first treatment agent is Hydrogen Peroxide. However, an operable first treatment agent may be selected from the group including (Hydrogen peroxide, Sodium Peroxide, Peracetic acid, Ammonium quaternary compounds, Alcohol in general, Benzyl alcohol, Sodium Hypochlorite, Acetic acid, glycolic acid, Silver Nitrate, and Silver citrate). An operable second treatment agent may be selected from that same group.

Figure 32:
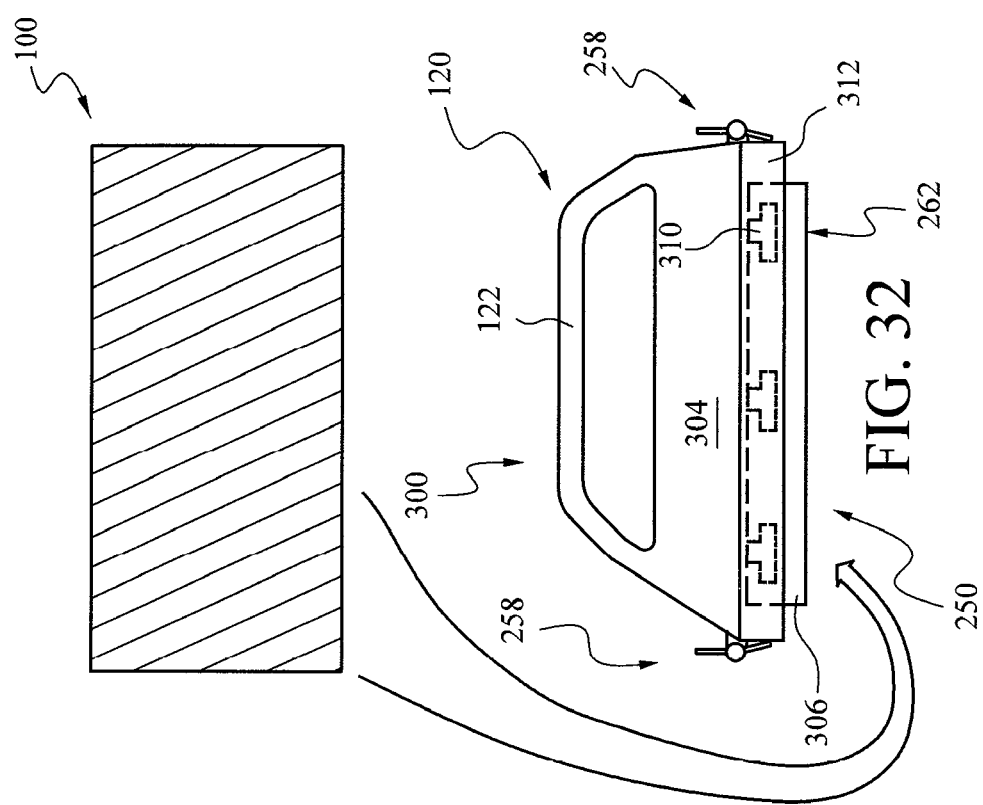
FIG. 32 is an exploded assembly view of a wipe in combination with another embodiment of a wipe holder having a dispensing reservoir.

The embodiment indicated generally at 300 in FIG. 32 includes an alternatively structured wipe-holder 120 configured to receive one of a plurality of disposable, single-use wipes 100. As with certain previously-described embodiments, a wipe 100 may be installed in registration on body 304 by affixing opposite ends of the wipe to respective clamp mechanisms 258, like installing a sheet of sandpaper on a powered sander. Alternative wipe-affixing mechanisms will be readily apprehended by one of ordinary skill. The handle 122 may be rigidly affixed to the body 304 (as illustrated) or may be pivotally or even removably affixed, e.g., to reduce volume during shipping. In any case, it is desirable for handle 122 to provide a user hand-gripping portion disposed substantially in parallel to a wipe-support surface 262.

A difference between illustrated embodiment 300 and previously described embodiments is the arrangement of the applicator of energized treatment agent, generally 250. Embodiment 300 includes a reservoir 306 of a first treatment agent structured to dispense the first treatment agent in a vapor phase. The first treatment agent combines with a second treatment agent carried by a wipe 100 to synergistically create an energized treatment agent in-situ, or at the time and place of use of the wipe 100 to clean or disinfect a surface. By synergistically, it is meant that a first treatment agent is selected to combine with a second treatment agent to form a third treatment agent having enhanced biocidal efficacy compared to either the first or second treatment agent, alone. In the illustrated embodiment 300, transfer of the first agent to a wipe 100 occurs by direct contact between the support surface 262 of reservoir 306 and an installed wipe 100. The first treatment agent may be essentially off-gassed from reservoir 306 and into the installed wipe 100 at the support surface 262.

In an alternative arrangement within contemplation, reservoir 306 may include an absorbent element that up-takes treatment agent in a fluid phase, and also dispenses that treatment fluid in a fluid phase on-demand, e.g., under physical pressure on a sponge. In that case, reservoir 306 may include a sponge element, such as a cellulose or polymer sponge, and the first treatment agent is applied in liquid form to the wipe.

Many ways to hold a reservoir 306 in registration with a body 304 are within contemplation, and will occur to one of ordinary skill. A preferred arrangement provides a structural interference between structure associated with body 304 and structure associated with reservoir 306, and a retaining mechanism to resist decoupling of those elements. Desirably, the installed reservoir 306 disposes a wipe support surface 262 proud of the body 304 to ensure that a wipe 100 carried there-on will contact a surface to be cleaned or disinfected.

The illustrated embodiment 300 includes a plurality of T-slots 308 in reservoir 306 that install in registration on cooperating T-elements 310 carried by body 304. The T-elements 310 form a structural interference with T-slots 308 when the reservoir 306 is installed in registration on a body 304. The retaining mechanism includes skirt 312, which may be vertically or rotationally displaced by a user to permit transverse motion of the reservoir 306 with respect to body 304. With the skirt 312 out of the way, the reservoir 306 may be installed or removed from the body 304, e.g., for replacement or recharging of the reservoir 306. After a reservoir 306 is installed, skirt 312 may be repositioned and affixed to prevent decoupling reservoir 306 from body 304.

A reservoir 306 may be structured to imbibe or uptake one or more liquid treatment agent, and subsequently dispense that treatment agent in liquid or vapor phase. A workable reservoir 306 may include an adsorbent material, and/or a material that up-takes a liquid treatment agent through a diffusion, or other essentially atomic, or molecular-scale process. Sometimes, a reservoir may include an absorbent element, such as a cellulose or polymer sponge, that can absorb liquid treatment agent and subsequently dispense that treatment agent on demand in a liquid phase.

Materials that may be included in a reservoir 306 encompass polymers, rubber, or rubber-like material (particularly styrene-based polymer or rubber, butadiene-based polymer or rubber, gum rubber, and thermoplastic polyurethane (TPU)), and high surface area (HSA) materials such as activated carbon, activated Alumina, activated Titanium oxide, (e.g., activated ceramics), metal/organic high surface area compounds, high surface area Silica, zeolites, molecular sieves, and the like. It is within contemplation that a reservoir may encompass a mix of different materials, such as a mix of absorbent and adsorbent materials. A mix of carrier materials for a reservoir 306 may be configured to provide a desired storage capacity and release rate capability for one or more agent.

High surface area materials may be fabricated and used as powders, granules, beads, chunks, sheets, and/or formed into particular functional structures, and the like. By high surface area, it is intended to mean a material having surface area greater than 10 $m^2/g$. It is generally preferred for HSA materials to be greater than 100, 200, 300, 400, 500, and/or 600 $m^2/g$. HSA materials having surface area of 2,000 or even 10,000 $m^2/g$, or even more, are within contemplation.

Portion(s) or the entirety of an exemplary reservoir may be manufactured by way of injection molding. A currently preferred reservoir 306 is made as a substantially unitary element from SBR rubber.

Figure 33:
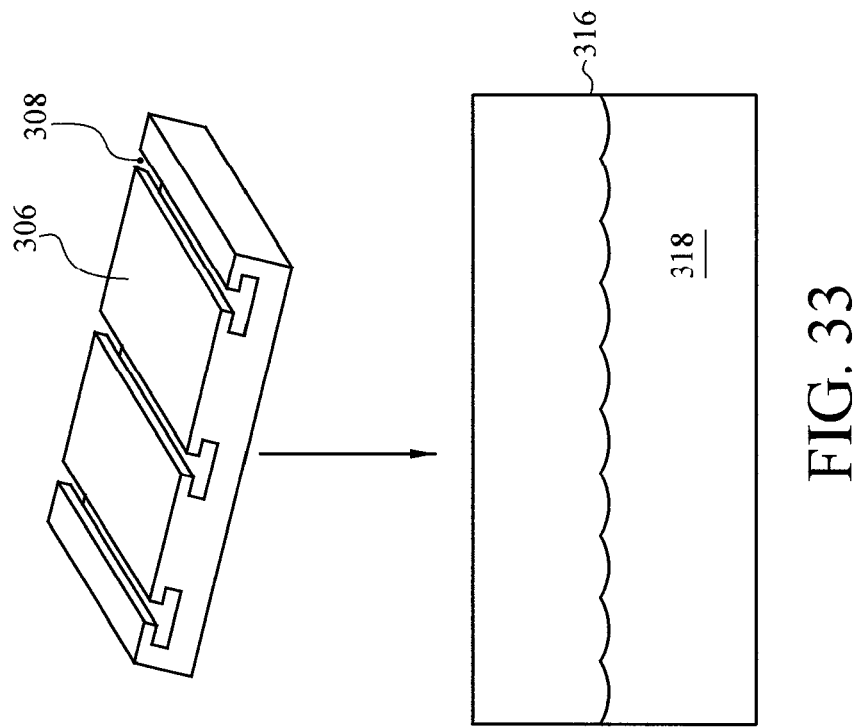
FIG. 33 is a side view of a charging operation for a reservoir such as that illustrated in FIG. 32.

As illustrated in FIG. 33, a reservoir 306 may be charged (or recharged) by placing the reservoir 306 into a container 316 holding a quantity of treatment agent 318. Certain embodiments may be sufficiently charged in a few hours at room temperature. Typically, no elevated temperature is required, although an elevated temperature may reduce charging time. A reservoir 306 made entirely from SBR can be charged sufficiently overnight in a container of acetic acid (e.g., household vinegar) at room temperature to operate synergistically with about 3 to perhaps 50 (or more) wipes that individually carry a hydrogen peroxide treatment agent. By room temperature, it is intended to encompass room air temperature of between about 20° C. and about 50° C. (e.g., about 65° F. to about 125° F.), and the fluid is disposed in the room and typically allowed to come to approximate thermal equilibrium.

Figure 34:
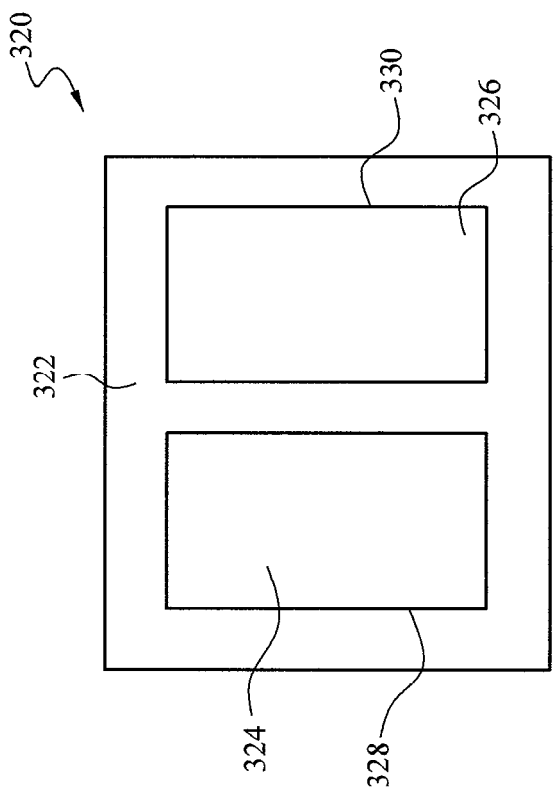
FIG. 34 is a plan view of an alternative wipe.

FIG. 34 illustrates a plan view of an alternative wipe generally indicated at 320. Wipe 320 includes a flexible substrate 322 carrying first compartment 324 and second compartment 326. Other embodiments within contemplation may include one or more additional compartment. Workable substrates may be embodied as woven or nonwoven cloth, fiber or polymer, and the like. Exemplary substrates include cloth, rags, or commercially available paper towels and similar structures. Desirably, the substrate and compartments are structured in harmony to permit operably folding or arranging the wipe to place the compartments in functional position to activate the first and second agents. One functional juxtaposed arrangement is nonexclusively illustrated in FIG. 35.

A workable compartment 324, 326 generally confines a first agent to resist undesired or premature combination of the first agent with a second agent carried in an adjacent compartment. A workable compartment also permits such combination at a time and place of desired use of the wipe 320 to clean, disinfect, sterilize, or deodorize an object. It is preferred for compartments and substrates to be porous to permit fluid flow.

As illustrated in FIG. 34, compartment 324 includes a boundary 328 inside of which the first agent is generally confined. A similar boundary 330 generally confines a second agent in association with compartment 326. A workable boundary may be provided, in-part, by a pocket-forming layer, or may be defined by a simple spacing on the substrate 322 between the agents, or be structured like a dam to resist in-plane flow or travel of an agent. It is within contemplation that certain embodiments may include first and/or second agents that are simply impregnated into, or otherwise carried by, just the substrate.

Figure 35:
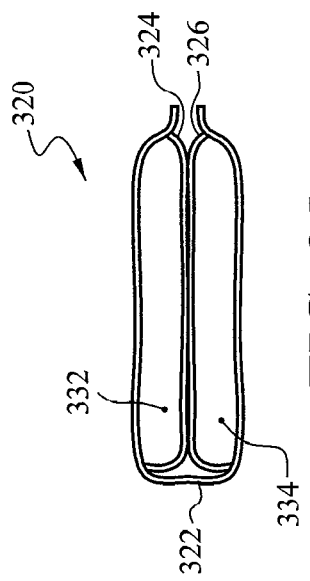
FIG. 35 is an end view of the wipe in FIG. 34, but folded to a deployment condition.

With reference to FIG. 35, first compartment 324 may be embodied as a fluid-porous bag in which is generally confined a first treatment compound or agent 332, such as Sodium Percarbonate ($Na_2CO_3$). In an exemplary embodiment, the agent 332 may be provided in suitable dry form, such as powdered. Second compartment 326 may similarly be embodied as a fluid-porous bag to generally confine high surface area (HSA) material. A HSA material is defined as having a surface area greater than 10 $m^2/g$. Exemplary HSA material includes activated Alumina or carbon, molecular sieves, zeolites, certain ceramics, nano-sized particulate material, and the like. The HSA material may be provided in substantially solid, powder, bead, or particulate form, and can operate as a carrier of a second treatment agent 334, such as acetic acid (e.g., vinegar), or glycolic acid. In certain alternative embodiments, a second treatment agent 334 may simply be provided by a damp compartment 326, or damp portion of a substrate 322.

When combined with a fluid like water, the first and second treatment agents of a wipe 320 may combine to form peracetic acid. In the case where the second treatment agent 334 is acetic or glycolic acid carried in HSA material, the HSA material preferentially displaces the acid to adsorb water, there-by discharging the acid for use as an active agent. Therefore, wipe 320 may be dipped in water, folded, and used to clean, deodorize, disinfect, or sterilize a surface of an object with a first treatment agent including peracetic acid that is formed at the time and place of use of the wipe 320. A second treatment agent in the present example is excess Hydrogen peroxide.

It is within contemplation that Hydrogen peroxide may be adsorbed into HSA material that is carried by a wipe 100, and an active agent such as acetic acid or glycolic acid may be applied (e.g., sprayed) onto the wipe 100. The HSA material preferentially displaces the Hydrogen peroxide to adsorb water or moisture from the spray, there-by discharging the Hydrogen peroxide for use as another active agent. The acetic or glycolic acid carried in the spray may react with a portion of the displaced Hydrogen peroxide to form peracetic acid as a third active agent.

A similar peracetic acid-forming embodiment may be created using the structure illustrated in FIGS. 24 and 25. In such an alternative embodiment, a wipe 106A may be embodied as a commercially available damp Hydrogen peroxide wipe. Hydrogen peroxide may be regarded as a first agent. Wipe 106B may be a similarly structured damp wipe substrate that carries an acid, such as acetic acid, vinegar, or glycolic acid. The acid, e.g., acetic acid, may be regarded as a second agent. Acetic or glycolic acid combines with a portion of Hydrogen peroxide at the time and place of use of the combined wipes 106A and 106B to form peracetic acid as a third agent. The combined damp wipes 106A and 106B may therefore be used to clean, disinfect, deodorize, or sterilize a surface with a combination of agents including Hydrogen peroxide and peracetic acid.

It is within contemplation that one or more wipe, or one or more agent used in a combination embodiment such as embodiment 200, may be stored in dry form. As used herein, "dry form" means that an agent feels dry to human touch. An exemplary dry agent encompasses liquid acetic or glycolic acid adsorbed into HSA material, which has a resulting surface that feels dry to the touch. Sometimes, acetic or glycolic acid may be directly provided on a wipe in dry compound form. In use, a fluid such as water may be applied to the dry wipe or portion thereof (or to two or more combined wipe substrates) at the time and place of use to create a desired chemical reaction, e.g., form or yield peracetic acid and/or Hydrogen peroxide.

Glycolic acid (sometimes known as hydroacetic acid or hydroxyacetic acid) has a chemical formula $C_2H_4O_3$ (also written as $HOCH_2CO_2H$). This compound is colorless, odorless, and naturally hygroscopic. The crystalline solid form at room temperature is highly soluble in water. For purpose of this disclosure, it is believed that the physical state of a particular material (e.g., solid or liquid) will be logically apparent. Without more, use of the material name alone is typically intended to encompass both solid and liquid phase states.

Figure 36:
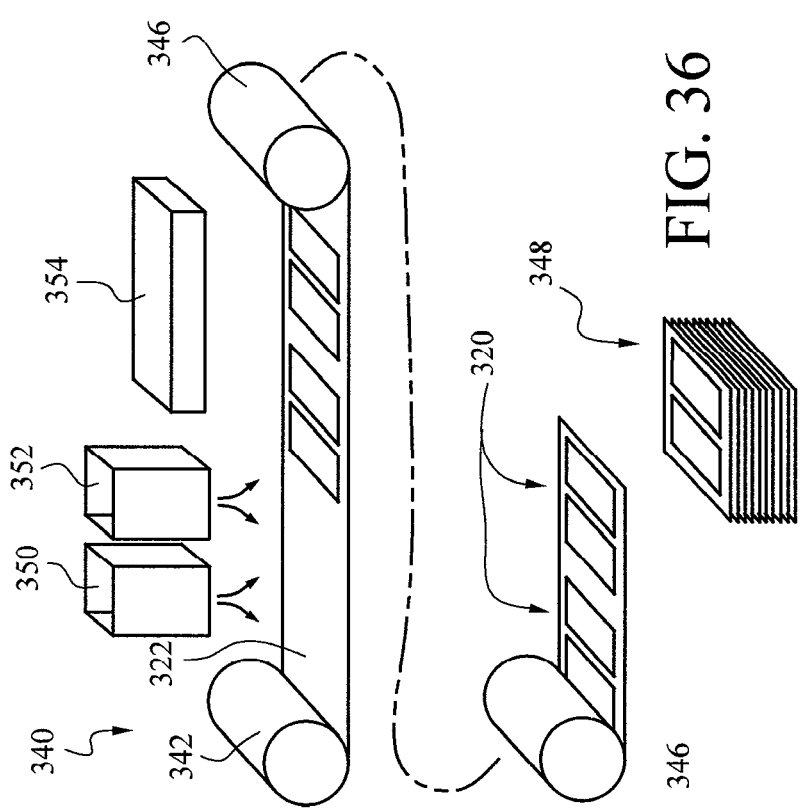
FIG. 36 illustrates a manufacturing process that may be employed to create a wipe according to certain aspects of the invention.

A method to manufacture a wipe, such as wipe 320, is illustrated generally at 340 in FIG. 36. A feed roll 342 provides a ribbon of substrate material 320. The ribbon may be spooled onto an intermediate take-up roll 346, or individual wipes 320 may be directly processed for packaging, as illustrated generally at 348. In any case, the ribbon may be arranged for indexed travel past a first applicator 350 of a first agent and a second applicator 352 of a second agent, which applicators apply respective agents into respective compartments 324, 326 (see FIG. 34). Alternatively, one or more of applicators 350, 352 may be structured to coat, imprint, emboss, embed, impregnate, or otherwise install an agent in registration on the substrate film ribbon in a desired configuration. Further processing of the ribbon, such as with application of heat by a heater 354, may be included in the manufacturing process.

Figure 37:
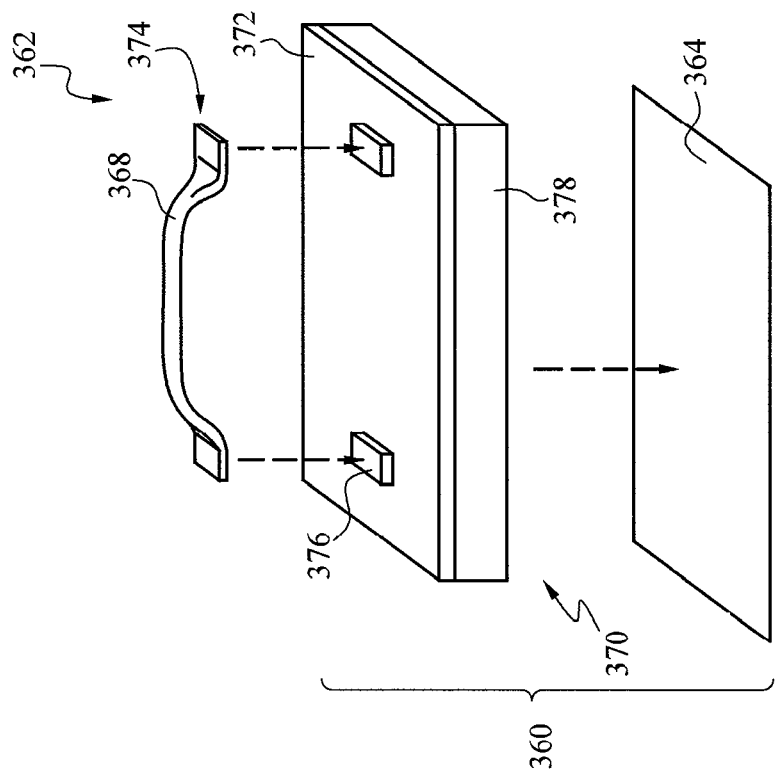
FIG. 37 is a view in perspective of an alternative wipe holder and wipe.

FIG. 37 illustrates another embodiment structured according to certain principles of the invention and indicated generally at 360. Embodiment 360 includes a handle assembly, generally 362 and a wipe 364. The handle assembly 362 may simply be placed onto a wipe 364 and employ friction there-between to allow using the handle 362 (and wipe 364) to scrub a surface, or the wipe 364 may be affixed in some way to the handle assembly. Desirably, a handle portion 368 of the assembly 362 is disposed substantially in parallel to a wipe support surface. An exemplary wipe 364 includes a commercially available disposable damp wipe that carries Hydrogen peroxide. A preferred embodiment 360 is structured to generate peracetic acid at the time of use of the wipe 364.

The handle assembly 364 illustrated in FIG. 37 includes a handle 368, and a reservoir, generally 370. A workable reservoir 370 provides a storage space from which an active first agent may be applied to an associated wipe 364 (and may sometimes form a third agent, e.g., peracetic acid, in combination with a second agent carried by wipe 364) for use in cleaning, deodorizing, disinfecting, or sterilizing an object.

A reservoir 370 may be removably affixed to a handle 368, or may have intervening structure to make a robust structural connection, such as a top plate 372. In the illustrated embodiment, handle 368 is flexible, and handle ends, generally 374, may be received in respective socket structures 376 that are affixed to a relatively stiff top plate 372. A workable stiff top plate 372 may be made from a sheet of about 1/16 or 1/8 inch thick plastic, such as PVC, or the like. Alternative attachment of a handle to a reservoir is within the capability of one of ordinary skill. A permanently affixed handle is also within contemplation.

A workable reservoir 370 includes a carrier element 378 in which to hold a quantity of a treatment agent, and permits dispensing that agent on-demand to a wipe. Top plate 372 may be characterized as a body, and carrier element 378 may be considered as being carried by the body with a wipe-support surface portion being disposed proud of the body to contact a wipe. In that configuration, a disposable wipe carried there-on or in contact there-with will contact a surface to be cleaned or disinfected, and the wipe will be compressed into contact with the support surface.

One workable carrier element 378 is an absorbent sponge, such as a commercially available cellulose sponge, to absorb and subsequently emit fluid agent on demand (e.g., to emit fluid agent onto a surface to be treated upon compression of the sponge to pass fluid through the wipe and onto the surface).

Another workable carrier element 378 includes HSA material, or rubber and rubber-like materials such as thermoplastic Polyurethane (TPU), styrene-based and/or butadiene-based rubbers, and the like. Certain carrier material elements 378 adsorb, imbibe, or otherwise uptake fluid with a molecular diffusion or other small-scale process. Sometimes, fluid carried by the wipe (and enhanced by action of an agent carried in the reservoir) may be emitted onto the surface to be treated by way of compression of the wipe between the reservoir and the surface. Fluid carried by the wipe may enhance extraction of an agent from the reservoir or carrier element 378 by preferential exchange of a portion of the wipe's fluid into the carrier material to release one or more agent from the carrier. A carrier element 378 may be loaded with an agent by way of absorption, adsorption, molecular diffusion, and any other mechanism operable to place an agent in association with the carrier for removal on-demand to form an activated wipe.

FIG. 38 illustrates another embodiment, generally indicated at 390, structured according to certain principles of the invention. Embodiment 390 includes a handle assembly, generally 392, that interfaces with or is associated with (as indicated by dashed line 391) a wipe 364 to permit use of the handle 394 to move the wipe 364 to scrub a surface of an object. Sometimes, the handle assembly 392 may simply be placed on top of a loose wipe 364 to enable scrubbing. Other times, the handle assembly 392 may be affixed to a wipe 364 to enable scrubbing. A preferred wipe 364 is a commercially available pre-moistened (or damp) cleaning wipe that carries Hydrogen peroxide as a first surface-treatment agent. A similar wipe structured as described above is also workable. The illustrated handle assembly 392 provides a second treatment agent to combine with a portion of the first treatment agent and form a third treatment agent (preferably, the third treatment agent is peracetic acid).

Handle assembly 392 includes an access opening, generally 396, to permit installation and removal of a cassette 398. Cassette 398 is structured to hold a quantity of a liquid treatment agent, such as a mild acid or other effective agent, for application of the treatment agent to a wipe 364. A preferred cassette 398 is refillable. A preferred mild acid includes acetic acid, vinegar, and/or glycolic acid.

In the illustrated embodiment 390, an installed cassette 398 is placed into operable association with an actuator, such as illustrated thumb button 400, to permit application of a dose of agent onto a wipe (as generally indicated by cloud 402). A dose may be applied as a mist, stream, or any other workable arrangement to distribute an agent carried in the dose in operable harmony with the wipe. The actuator 400 may be embodied in a plurality of alternative forms, including as a trigger disposed for finger-actuation, and the like, as will be well known by one in the art.

Sometimes, the handle assembly 392 may be used to spray a dose 402 of agent (e.g., liquid acetic acid or glycolic acid) onto a wipe 364 prior to associating the wipe 364 with the handle 394 for scrubbing. Other times, one or more dose-discharging nozzle may be configured to apply a dose 402 to a wipe 364 that is already associated with the handle assembly 392 to permit scrubbing. In certain cases, the handle assembly 392 may be used to apply a dose 402 to a wipe, and the wipe may be used for cleaning separately from the handle assembly 392.

The embodiment in FIG. 39 illustrates a wipe, generally indicated at 410, including another membrane-like substrate 322 and a fluid-permeable pocket 412. Pocket 412 is structured to confine one or more chemical compound. Typically, pocket 412 carries at least a pair of chemical compounds in dry form that may be either mixed together or segregated in some way that permits combination of their liquidized forms. As illustrated, a first chemical compound is generally indicated at 414, and a second chemical compound is generally indicated at 416. Dry chemical compounds may be provided in chunks, granules, powders, and the like.

One operable set of dry chemical compounds includes Sodium percarbonate and glycolic acid. In use of such a wipe 410, a user simply applies water, and uses the wipe 410 to scrub or wash a surface. For non-limiting examples, the wipe 410 may be dipped in, or sprayed by, water. The wetted wipe 410 can inherently make Hydrogen peroxide and peracetic acid due to wetting the one or more compounds carried in the pocket 412. For one example, water and Sodium percarbonate may combine to form excess Hydrogen peroxide, and further addition of liquid glycolic acid combined with (typically a portion of) the Hydrogen peroxide produces peracetic acid as well.

The embodiment indicated generally at 420 in FIGS. 40 and 41 includes a wipe, generally 100, and a wipe holder or wipe manipulator, generally 422. A preferred wipe 100 includes a commercially available damp membrane-like sheet 424 that carries Hydrogen Peroxide. A workable wipe manipulator 422 may be embodied as a glove 426 (as illustrated) or as a mitten, among other configurations. Glove 426 includes thumb 428 and index finger 430 that are identified here to assist in orienting structure in different views.

The wipe manipulator 422 includes at least one reservoir 432, in which a bulk portion of treatment agent may be held. With reference to FIG. 41, reservoir 432 is arranged to deliver treatment agent through conduit 434 to a dispersion element 436. The dispersion element 436 serves to distribute treatment agent from conduit 434 for application to a surface of a wipe 424. An exemplary dispersion element 436 may be formed by an absorbent device such as a cellulose sponge, or a wicking or capillary device such as a fiber mat, and the like. A discharge mechanism, generally indicated at 438, is provided to urge travel of treatment agent toward the dispersion element 436. An exemplary discharge mechanism 438 includes a plunger or pump 440 that may be mechanically activated, such as by slide lever 442. Treatment agent may be distributed by one or more conduit 434 to a plurality of positions scattered over the area of a dispersion element 436, to facilitate formation of treatment agent across a significant area of a wipe 424.

With reference now to FIG. 42, the wipe manipulator generally indicated at 422' includes a glove 426, similar to that illustrated in FIGS. 40 and 41. A reservoir 432 carried by glove 426 defines a volume 444, in which to hold a treatment agent. A pump 446 is arranged in fluid communication with the treatment agent to urge travel of treatment agent toward dispersion element 436. Pump 446 may be actuated on user-demand by actuation of normally-open switch 448. A user may close switch 448 by pressing it between a fingertip and the surface to be treated, and thereby cause actuation of the pump 446. Switch 448 is operably connected to pump 446 by way of wires 450. Electronics and other operational controls, generally 452, may be carried in association with reservoir 432 to alternatively or additionally control automated operation of pump 446 according to e.g., a desired discharge rate, or under certain user-controlled or predefined parameters or input(s).

A first treatment agent may be formed in a wipe responsive to combination of a second treatment agent delivered by a dispersion element 436 and third treatment agent that may be carried in the wipe, or may also be supplied by a wipe manipulator. Of note in the cross-section in FIG. 42, a wipe manipulator such as 422' includes a safety mechanism including a structural barrier normally disposed between a user's hand and a location of formation of the first treatment agent. That structural barrier includes the palm portion of the glove 426. FIG. 42 also illustrates a volume 454 defined by the wipe manipulator 422'. Volume 454 is defined as a substantially enclosed volume inside of glove portion 426 and is configured to receive a user's hand prior to allowing formation of a first treatment agent in a wipe.

With reference now to FIG. 43, a wipe manipulator 422 may be structured to carry and apply a second treatment agent for combination with a third treatment agent, the second treatment agent and third treatment agent combining to form a first treatment agent in wipe 424. Preferably, the wipe manipulator includes some sort of safety mechanism to resist formation of the first treatment agent until a user's hand is protected from contact with the first treatment agent. In FIG. 42, the safety mechanism includes an effective physical barrier provided by the palm portion of glove 426. A workable glove 426 may be waterproof and is desirably resistant to attack or damage caused by treatment agents.

Additionally, it is desirable that a wipe manipulator further includes a wipe support surface, generally 456, that is sufficiently transversely flexible as to enable using the wipe support surface 456 to engage a wipe 424 with curved structures such as cylindrical objects forming bed rails, and stands to hold medical devices. For example, a wipe manipulator 422 may enable wrapping a wipe 424 to engage wipe 424 with about 90, 180, 270, or more degrees around the circumference of a curved surface of a rod 458. An exemplary such rod 458 may have a radius R of about ⅛ inch, ¼ inch, ⅜ inch, ½ inch, 2 inches, or even more. Preferably, substantially that amount of transverse flexibility is provided by a wipe support surface 456 in two orthogonal directions. Desirably, the transverse flexibility of the wipe support surface 456 approximates a degree of conformity provided by a human hand covered by a surgical glove. It is further desirable for the wipe support surface and any other intervening protective structure(s) to transmit tactile feedback to a user to verify contact with the treated surface by a wipe.

With reference now to FIGS. 44 and 45, a wipe manipulator 422" comprises an exposed wipe support surface 464 of a first reservoir 432 to support a wipe 424. The illustrated reservoir 432 is formed from a material capable of temporarily and internally holding a second treatment agent to permit release of the second treatment agent for combination in the wipe with a third treatment agent, the second treatment agent and third treatment agent combining to form a first treatment agent. Release of the second agent may variously be effected by off-gassing a treatment agent in vapor form, or by direct fluid flow of a solution including the second treatment agent. The first treatment agent may be unsafe for direct contact with human skin, but is desirably toxic to bacteria and microbes.

FIG. 45 also illustrates a volume 454 defined by the wipe manipulator 422". Volume 454 is defined as a substantially enclosed volume inside of glove portion 426 and is configured to receive a user's hand, and to resist contact between the hand and a first treatment agent that is formed, or is being formed, in a wipe. Desirably, glove portion is made from a material that may be waterproof or water resistant, and is resistant to damage from contact with any treatment agents.

It is further desirable that reservoir 432 and glove 426 cooperate to form a wipe support surface 464 that is transversely flexible to enable treating curved surfaces. A workable reservoir may include material that can imbibe a treatment agent (or a fluid including the treatment agent), and subsequently release the treatment agent for combination with element(s) or compound(s) in a wipe. Materials of composition for a workable reservoir 432 include absorbent materials, such as a sponge including a cellulose sponge, woven and nonwoven fibrous elements such as cloth or felt, and certain polymer or rubber materials. Other workable materials are described above with reference to alternative embodiments.

With reference again to FIG. 41, a wipe manipulator may simply be placed on top of a wipe 424, trapping the wipe 424 between a distribution element 436 and the surface to be treated. Friction between the wipe and manipulator 422 is typically sufficient to enable manipulation of the wipe to treat the surface.

It is within contemplation to alternatively provide a wipe and wipe manipulator with cooperating structures to ensure workable association with, operation of the wipe by, the manipulator. One such cooperating arrangement includes forming a wipe as a pocket or mitten 252 (e.g., see FIG. 28). For another example, FIG. 46 illustrates a space 468 that may be formed in a wipe formed by fastening a pair of wipes 424 along three edges. Resulting space 468 may then receive a wipe manipulator. It is further within contemplation to provide cooperating structures to secure a wipe to a wipe manipulator. Certain such structures nonexclusively include hook-and-loop fasteners, clamping mechanisms, fastening straps, interference-creating structures, and the like.

One method for cleaning/treating (e.g., deodorizing, disinfecting, or sterilizing) a surface includes the steps of: providing a holder structured in harmony with a disposable wipe to create micron- or nano-sized particles of a first treatment agent carried by the wipe and selected from the group consisting of (Hydrogen peroxide, Sodium Peroxide, Peracetic acid, Ammonium quaternary compounds, Alcohol (e.g., Benzyl or other effective alcohol), Sodium Hypochlorite, Acetic acid, glycolic acid, Silver Nitrate, and Silver citrate), and/or to create hydroxyl or other chemical radicals from a portion of the first chemical treatment agent; placing a disposable wipe in operable registration with the holder; and treating a surface of an object by activating the holder to energize a portion of the first treatment agent and wiping the object with the disposable wipe.

Another operable treatment method may include providing an applicator structured to create a fog of micron- or nano-sized particles of a first chemical treatment agent selected from the group (Hydrogen peroxide, Sodium Peroxide, Peracetic acid, Ammonium quaternary compounds, Alcohol, Sodium Hypochlorite, Acetic acid, glycolic acid, Silver Nitrate, and Silver citrate), and/or to create hydroxyl or other chemical radicals from a portion of the first chemical treatment agent; treating a surface of an object by applying the fog and/or chemical radicals onto the object with the applicator; and wiping the surface with a disposable wipe.

Another operable treatment method may include providing a wipe that may be activated at the time and place of use to create peracetic acid. This method may include the step of wetting the wipe to activate the wipe. In an alternative method, the activation step may be effected by combining two or more substrates to form an activated wipe. In an alternative method, the activation step may be effected by combining two or more substrates, then applying a fluid such as water, to form an activated wipe. In an alternative method, the activation step may be effected by folding the wipe to place two reactive elements into operable juxtaposition to cause a chemical reaction, and then using the wipe to scrub the surface with a treatment agent including a product resulting from that chemical reaction.

The invention may be practiced in a method that may further include a pre-treatment step including application of a surface treatment to the surface to be treated. One surface treatment within contemplation enhances the hydrophilic status of the surface. An exemplary surface treatment may be selected from chemical surfactant, and plasma. Another surface treatment within contemplation includes a fog of micron- or nano-sized particles of a first chemical treatment agent selected from the group (Hydrogen peroxide, Sodium Peroxide, Peracetic acid, Ammonium quaternary compounds, Alcohol, Sodium Hypochlorite, Acetic acid, glycolic acid, Silver Nitrate, and Silver citrate; treating a surface of an object by applying the fog onto the object; and wiping the surface with a disposable wipe. In some cases, the applicator used in a method according to certain principles of the invention may be, or include, the disposable wipe.

While the invention has been described in particular with reference to certain illustrated embodiments, such is not intended to limit the scope of the invention. The present invention may be embodied in other specific forms without departing from its spirit or essential characteristics. For example, one or more element may be extracted from any described embodiment for use on its own, and/or combined with one or more element from any other embodiment to form an alternative embodiment according to certain principles of the invention. One or more element(s) may sometimes be redacted from certain embodiments to form alternative workable embodiments. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for cleaning, deodorizing, disinfecting, or sterilizing a surface of an object, comprising:
   a disposable wipe to apply a first treatment agent to treat the object, the disposable wipe to form the first treatment agent in or on the disposable wipe at the time and place of use of the disposable wipe, in combination with:
   a reusable wipe manipulator structured to temporarily couple with the disposable wipe sufficiently to move the wipe over the surface in a cleaning motion with the disposable wipe being in physical contact with the surface, the reusable wipe manipulator comprising a safety mechanism to resist formation of the first treatment agent until a user's hand is protected by a structural barrier from contact with the first treatment agent, wherein:
   the reusable wipe manipulator is structured to apply a second treatment agent for combination with a third treatment agent, the second treatment agent and third treatment agent combining to form the first treatment agent in or on each disposable wipe of a plurality of successive disposable wipes, and:
   the reusable wipe manipulator comprises a wipe support surface that is transversely flexible to accommodate wiping curved surfaces.

2. The apparatus according to claim 1, wherein:
   the reusable wipe manipulator comprises a first reservoir; and
   the first reservoir holds a quantity of a second treatment agent for combination with a third treatment agent carried by the disposable wipe, the second treatment agent and the third treatment agent combining to form the first treatment agent.

3. The apparatus according to claim 1, wherein:
the first treatment agent is selected from the group consisting of Hydrogen Peroxide, peracetic acid, Chlorine Dioxide, Sodium Hypochlorite, Hydroxyl radicals, Glutaraldehyde, Phenol, and a mixture of two or more elements from this group.

4. The apparatus according to claim 2, wherein:
the second treatment agent consists of an element selected from the group consisting of Acetic acid, vinegar, tetraacetylethylenediamine (TAED), and a mixture of two or more elements from this group;
the third treatment agent is Hydrogen peroxide; and
the first treatment agent is Peracetic acid.

5. The apparatus according to claim 1, wherein:
the second treatment agent comprises solid mixtures of Sodium acetate and Benzoic acid, or Sodium acetate and Citric acid;
the third treatment agent comprises Hydrogen Peroxide; and
the first treatment agent is Peracetic acid.

6. The apparatus according to claim 2, wherein:
the second treatment agent is Sodium Chlorite or Sodium Chlorate in liquid solution;
the third treatment agent is Citric acid or Hydrochloric acid; and
the first treatment agent is Chlorine Dioxide.

7. The apparatus according to claim 1, wherein:
the second treatment agent is an element selected from the group comprising UV light, Ferrous Sulfate, and Ozone;
the third treatment agent is Hydrogen Peroxide; and
the first treatment agent is Hydroxyl radicals.

8. The apparatus according to claim 2, wherein:
the first reservoir holds a bulk quantity of a second treatment agent in liquid solution, and further comprising:
a discharge mechanism operable on demand by a user to dispense the second treatment agent at a desired rate and/or quantity in the form of a plurality of successive doses to permit application of one or more dose to each individual disposable wipe of the plurality of successive disposable wipes.

9. The apparatus according to claim 2, wherein:
the first reservoir holds a quantity of a second treatment agent and is structured to permit off-gas application of the second treatment agent from the first reservoir to combine with a third treatment agent to form the first treatment agent in or on each disposable wipe of the plurality of successive disposable wipes.

10. The apparatus according to claim 1, wherein:
the reusable wipe manipulator comprises a portion of a glove or mitten.

11. The apparatus according to claim 1, wherein:
the reusable wipe manipulator comprises a discharge mechanism operable on demand by a user to dispense the second treatment agent at a desired rate and/or quantity.

12. An apparatus for cleaning, deodorizing, disinfecting, or sterilizing a surface of an object, comprising:
a disposable wipe to apply a first treatment agent to treat the object, the disposable wipe to form the first treatment agent in or on the disposable wipe at the time and place of use of the disposable wipe; and
a reusable wipe manipulator configured to temporarily couple with the disposable wipe sufficiently to move the disposable wipe over the surface in a cleaning motion with the disposable wipe being in physical contact with the surface, the reusable wipe manipulator comprising a safety mechanism comprising a structural barrier normally disposed between a user's hand and a location of formation of the first treatment agent in or on each disposable wipe of a successive plurality of individual disposable wipes, wherein:
the reusable wipe manipulator is structured to carry and apply a second treatment agent for combination with a third treatment agent, the second treatment agent and third treatment agent combining to form the first treatment agent, the reusable wipe manipulator further comprising a wipe support surface that is sufficiently transversely flexible as to enable using the wipe support surface to wrap each disposable wipe of the successive plurality of individual disposable wipes around about 270 degrees of the circumference of a curved surface of a ½ inch diameter rod.

13. The apparatus according to claim 12, wherein:
the reusable wipe manipulator is structured as a glove or mitten to receive a human hand in a substantially enclosed volume; and
the reusable wipe manipulator comprises an exposed surface of a first reservoir to support a wipe and formed from a material capable of temporarily and internally holding a second treatment agent to permit off-gas release of the second treatment agent for combination with a third treatment agent in the wipe, the second treatment agent and third treatment agent combining to form the first treatment agent.

14. The apparatus according to claim 1, wherein:
the first treatment agent is unsafe for direct contact with human skin.

15. The apparatus according to claim 1, wherein:
the reusable wipe manipulator carries a first reservoir and a second reservoir, the first reservoir to hold a bulk quantity of a fluidized second treatment agent, the second reservoir to hold a quantity of a third treatment agent, the reusable wipe manipulator to dispense individual dose quantities of the second treatment agent and individual dose quantities of the third treatment agent for combining in or on each of a plurality of successive individual disposable wipes to form the first treatment agent in or on each of the plurality of successive individual disposable wipes; and
the reusable wipe manipulator comprises a conduit in fluid communication at a first conduit end with the first reservoir to convey the second treatment agent for application of the second treatment agent to each of the plurality of successive individual disposable wipes.

16. The apparatus according to claim 15, further comprising:
a pump to urge on-demand transmission of the second treatment agent through the conduit; and
a dispersion element carried by the reusable wipe manipulator, the dispersion element being disposed in fluid communication with a second conduit end, the dispersion element to distribute treatment agent to a surface of a disposable wipe.

* * * * *